US010493027B2

(12) United States Patent
Hariharan

(10) Patent No.: US 10,493,027 B2
(45) Date of Patent: *Dec. 3, 2019

(54) CHEMICALLY STABLE COMPOSITIONS OF A PHARMACEUTICAL ACTIVE AGENT IN A MULTI-CHAMBERED DELIVERY SYSTEM FOR MUCOSAL DELIVERY

(71) Applicant: MUCODEL PHARMA LLC, Greensboro, NC (US)

(72) Inventor: Madhu Hariharan, Greensboro, NC (US)

(73) Assignee: MUCODEL PHARMA LLC, Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/682,764

(22) Filed: Aug. 22, 2017

(65) Prior Publication Data

US 2017/0348224 A1  Dec. 7, 2017

Related U.S. Application Data

(63) Continuation-in-part of application No. 15/430,038, filed on Feb. 10, 2017, which is a continuation-in-part of application No. 14/820,081, filed on Aug. 6, 2015, now Pat. No. 9,682,039.

(60) Provisional application No. 62/034,496, filed on Aug. 7, 2014.

(51) Int. Cl.

| A61K 9/00 | (2006.01) |
| A61K 31/485 | (2006.01) |
| A61M 5/19 | (2006.01) |
| A61K 6/08 | (2006.01) |
| A61K 9/06 | (2006.01) |
| A61K 9/08 | (2006.01) |
| A61K 9/107 | (2006.01) |
| A61K 31/407 | (2006.01) |
| A61K 31/5513 | (2006.01) |
| A61K 47/10 | (2017.01) |
| A61K 47/20 | (2006.01) |
| A61K 47/22 | (2006.01) |
| A61K 47/02 | (2006.01) |
| A61K 45/06 | (2006.01) |
| A61K 47/12 | (2006.01) |
| A61K 47/38 | (2006.01) |

(52) U.S. Cl.
CPC ............ *A61K 9/006* (2013.01); *A61K 9/0043* (2013.01); *A61K 9/06* (2013.01); *A61K 9/08* (2013.01); *A61K 9/107* (2013.01); *A61K 9/1075* (2013.01); *A61K 31/407* (2013.01); *A61K 31/485* (2013.01); *A61K 31/5513* (2013.01); *A61K 45/06* (2013.01); *A61K 47/02* (2013.01); *A61K 47/10* (2013.01); *A61K 47/12* (2013.01); *A61K 47/20* (2013.01); *A61K 47/22* (2013.01); *A61K 47/38* (2013.01); *A61M 5/19* (2013.01)

(58) Field of Classification Search
CPC ............ A61J 1/20; A61J 1/2089–2093; A61K 31/485; A61K 9/0043
See application file for complete search history.

(56) References Cited

U.S. PATENT DOCUMENTS

| 5,906,830 | A | * | 5/1999 | Farinas | ................ | A61K 9/7053 424/448 |
| 6,116,900 | A | | 9/2000 | Ostler | | |
| 6,284,765 | B1 | * | 9/2001 | Caffrey | ............... | A61K 9/0043 514/263.32 |
| 8,642,086 | B2 | | 2/2014 | Coady et al. | | |
| 9,192,570 | B2 | * | 11/2015 | Wyse | ................... | A61K 9/0043 |
| 2007/0166238 | A1 | | 7/2007 | Duggan | | |
| 2007/0208011 | A1 | | 9/2007 | Cloyd | | |
| 2008/0103169 | A1 | * | 5/2008 | Phillips | ..................... | A61J 1/20 514/303 |
| 2009/0023766 | A1 | | 1/2009 | Clarke | | |
| 2014/0005218 | A1 | | 1/2014 | Myers et al. | | |
| 2014/0008366 | A1 | | 1/2014 | Genosar | | |
| 2014/0088486 | A1 | | 3/2014 | Uhland et al. | | |
| 2014/0371210 | A1 | | 12/2014 | Battaglia | | |
| 2016/0038406 | A1 | | 2/2016 | Hariharan | | |
| 2016/0136157 | A1 | | 5/2016 | Wyse et al. | | |
| 2017/0348224 | A1 | | 12/2017 | Hariharan | | |

FOREIGN PATENT DOCUMENTS

| WO | 01/58447 A2 | 8/2001 |
| WO | 2009/046444 A2 | 4/2009 |
| WO | 2010/104494 A2 | 9/2010 |

OTHER PUBLICATIONS

International Search Report and Written Opinion of Appln. No. PCT/2018/017384 dated Apr. 6, 2018 in English.
Search Report EP Appln. No. 15829906.5 dated Dec. 22, 2017 in English.
Vishwas et al, Effect of Surfactants and pH on Naltrexone (NTX) permeation across buccal mucosa, Int. J. Pharm. Jun. 15, 2011 411 (1-2): 92-97.
International Search Report issued with Appln. No. PCT/US15/44033 dated Nov. 4, 2015.

* cited by examiner

*Primary Examiner* — H. Sarah Park
(74) *Attorney, Agent, or Firm* — Fitch, Even, Tabin & Flannery, LLP

(57) ABSTRACT

A kit for mucosally administering a metastable supersaturated solution of a pharmaceutical active agent to a human patient includes a first compartment comprising a first composition comprising a pharmaceutical active agent in solution at or below equilibrium solubility, and a second composition comprising an acidic buffer. The first and second compartments maintain separation of the first and second compositions during storage, and allow for mixing of the first and second compositions to form a supersaturated solution above equilibrium solubility of the pharmaceutical active agent for immediate mucosal administration to a human patient. In one embodiment, the second composition comprises an acidic buffer and the supersaturated solution has an acidic pH. Alternatively, the second composition comprises a basic buffer and the supersaturated solution has a basic pH.

7 Claims, 11 Drawing Sheets

Figure 11. Naloxone plasma concentration in humans by different routes of administration.
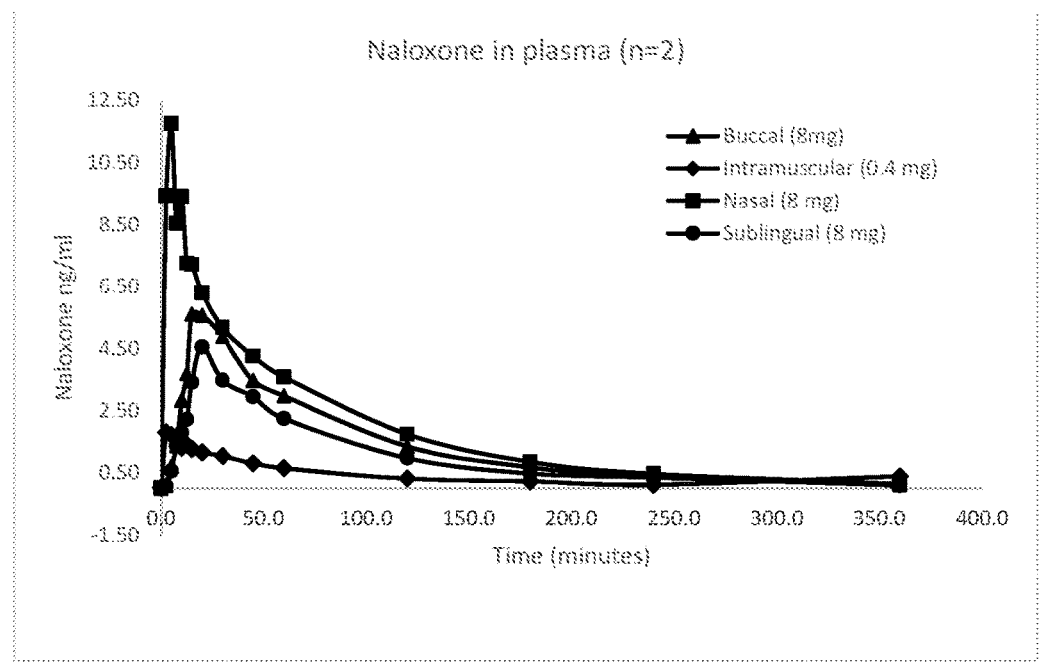
Figure 12: Comparison of nalbuphine buccal versus intranasal dosing
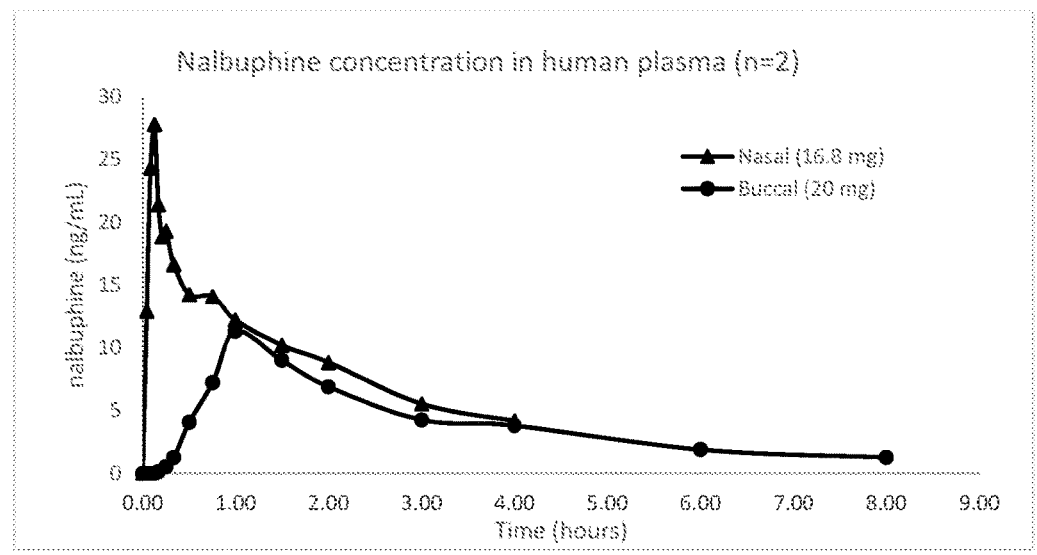

CHEMICALLY STABLE COMPOSITIONS OF A PHARMACEUTICAL ACTIVE AGENT IN A MULTI-CHAMBERED DELIVERY SYSTEM FOR MUCOSAL DELIVERY

CROSS-REFERENCE TO RELATED APPLICATIONS

This application is a continuation-in-part of application Ser. No. 15/430,038, filed Feb. 10, 2017, which is a continuation-in-part of application Ser. No. 14/820,081, filed Aug. 6, 2015, now U.S. Pat. No. 9,682,039, which claims the benefit under 35 U.S.C. § 119(e) of U.S. Provisional Application No. 62/034,496, filed Aug. 7, 2014, the entire disclosure of each of which is hereby incorporated by reference.

FIELD OF THE INVENTION

The present invention relates to pharmaceutically active drugs in general, and to rescue therapeutics, including without limitation opioid antagonists, and to improved buccal, gingival, sub-lingual, intranasal, ocular, vaginal and rectal absorption of pharmaceutically active drugs in general, including without limitation rescue therapeutics, and to kits for administering compositions containing such pharmaceutically active drugs.

BACKGROUND OF THE PRESENT INVENTION

Mucosal delivery is less often employed with rescue therapeutics because of challenges in effecting rapid mucosal delivery of therapeutically effective blood levels. The challenge of mucosal delivery of therapeutics has very plain real world implications for patients.

For example, the current mainline treatment for the treatment of breakthrough seizure control—particularly in pediatric patients—is Diastat®. Diastat® is a rectally administered diazepam gel. That a parent or guardian must take the time to disrobe a child in active seizure to rectally administer a rescue therapeutic speaks to both the reality of the challenge of oromucosal delivery (i.e. that there is not an oral alternative), and to the unmet medical need that is addressed by certain embodiments of the present invention. See, https://www.accessdata.fda.gov/drugsatfda_docs/ . . . /020648s008lbl.pdf and https://www.accessdata.fda.gov/drugsatfda_docs/label/2008/013263 s083lbl.pdf, the contents of which are incorporated herein by reference.

Migraine and post-operative pain are frequently treated with narcotic analgesics—because safer pharmaceutical agents like non-steroidal anti-inflammatory drugs cannot be absorbed rapidly enough and at sufficient blood levels to effectively treat the symptoms—despite the fact that narcotic analgesics carry a known risk of subsequent abuse and addiction.

Yet another example of an unmet rescue therapeutic need is the use of naloxone hydrochloride to treat opioid overdose. See, generally, https://pubchem.ncbi.nlm.nih.gov/compound/5284596, the content of which is incorporated herein by reference. The only current treatment options are injectable drugs (which present needle stick risk), and intranasal delivery (which may be contraindicated for certain patient populations).

Other unmet rescue therapeutic needs are rapid delivery of anxiolytics for panic attack and other anxiety disorders; anti-emetics for post-operative nausea and motion sickness; bronchodilators for anaphylactic shock; anti-hypertensives for emergency treatment of high blood pressure; and anti-allergenics for treatment of hypersensitivity and allergic reactions.

Naloxone hydrochloride is a specific and effective opioid antagonist which acts competitively at opioid receptors in the brain and has been found to have a wide variety of medical uses, for example, in reversing of the effects of therapeutic or overdose quantities of opioid narcotic drugs. Thus, intravenous, intramuscular or subcutaneous naloxone hydrochloride is used in diagnosis and treatment of opioid overdose and is also administered post-operatively to reverse central nervous system depression resulting from the use of opioids during surgery.

Naloxone is also used for treatment of overdose of illicit opioid narcotics. The most common method of treatment is the use of an injectable naloxone product (or the newer product EVZIO™) which are available in the United States. These injectable products are commonly used in emergency room settings, and are also sometimes carried by law enforcement officials to rapidly reverse opioid overdose. A nasally administered naloxone spray to deliver an emergency dose of naloxone is also available in some countries. In the USA, the injectable product is currently used along with Mucosal Atomization Device (MAD™). The USA has also approved NARCAN™ nasal spray. Injectable and nasal naloxone are effective but not adequately portable to be routinely and conveniently carried on one's person. Furthermore, training is required for the administration of these products which may limit their widespread availability and use. See, www.accessdata.fda.gov/drugsatfda_docs/label/2015/208411lbl.pdf, the content of which is incorporated herein by reference.

Moreover, there are certain questions of the reliability of intranasal delivery for certain patient populations, as more fully described in the Citizen Petition of Mucodel Pharma available here: https://www.regulations.gov/document?D=FDA-2017-P-0428-0001.

Some narcotic antagonists can also be used to dissuade addictive behavior. U.S. Pat. Nos. 8,673,355 and 7,749,542 and 7,419,686 and 7,172,767 and 6,696,066 and 6,475,494 and 6,277,384 teach the combination of an opioid antagonist and an opioid agonist to discourage patients from diverting the product for illicit parenteral use. However, these patents provide no teaching as to the delivery of an opioid antagonist by itself. Other patents related to the field of the present invention include U.S. Pat. Nos. 8,652,515, 8,524,275, 8,017,148, 7,842,307, 7,718,192, 7,682,634, 7,332,182, 7,144,587, 6,627,635, and 8,475,832. These patents and their contents are incorporated into this specification by reference and as if they were fully set forth herein.

U.S. Pat. No. 8,475,832 teaches the combination of an agonist and antagonist and discusses the use of buffers to limit the absorption of Naloxone in the oral cavity using a buffer with a pH of 3-4. However, there is neither a mention of optimizing the absorption of an antagonist, nor mention of how to stabilize the antagonist during storage. U.S. Pat. No. 7,682,634 teaches the use of seal coatings to keep the agonist and the antagonist separated. But again, this art is directed to a combination of the agonist (opioid) and the antagonist (naloxone). These patents and their contents are incorporated by reference in this specification and as if they were fully set forth herein.

Ionizable pharmaceutically active compounds may be classified by their charge state properties as either basic, acidic or zwitterionic. Generally speaking, acidic drugs tend to be more soluble at basic pH and basic drugs would be more soluble at acidic pH. In solution, basic drugs would have a larger fraction existing as the ionized/unprotonated species at a pH below their pKa. On the other hand, they would be predominantly unionized/protonated at a higher pH above their pKa. In solution, acidic drugs would have a larger fraction in the ionized state at higher pH while at lower pH the drug would be predominantly unionized. Bases include, inter alia, aliphatic amines, anilines, basic amides, amidines, guanidines and heterocyclic nitrogen atoms. Drugs with acidic groups include, inter alia, carboxylates, phenols, sulfonamides and also heterocyclic nitrogen atoms and less commonly phosphates, tetrazoles, thiols, alcohols carbamates, hydrazides, imides and sulfates.

The term pharmaceutically active agent herein includes free acids and free bases as well as their salt forms. Pharmaceutical salt refers to an ionizable drug that has been combined with a counter-ion to form a neutral complex. Converting a drug into a salt through this process can increase its chemical stability, render the complex easier to administer and allow manipulation of the pharmaceutically active agent's equilibrium solubility and pharmacokinetic profile. The term pharmaceutically active agent may also mean racemic mixtures of the left- and right-handed enantiomers of chiral drugs or a single purified enantiomer with biological activity.

It is generally accepted that the permeation of ionizable molecules follows the pH-partition theory as explained by Chen et al, A mechanistic analysis to characterize oromucosal permeation properties. Int. J. of Pharmaceutics 184 (1999) 63-72, using nicotine as a model substance. The pH-partition theory was proved from the observations that permeability, partition coefficient and diffusivity of nicotine, varied as a function of pH. The neutral unionized nicotine species had a higher permeability than the ionized species due to its higher partition coefficient and diffusivity via the transcellular pathway. It is generally understood that neutral molecules are more readily able to traverse non-polar lipidic membrane environments, whereas this process is energetically disfavored for charged compounds. Acid/base character and pKa values are thus generally considered important determinants for absorption and permeation, however it is recognized that other factors such as lipophilicity, molecular size, metabolic lability, hydrophilicity and efflux mechanisms can also influence absorption.

Vishwas, Rai, Hock S. Tan, Bozena Michniak-Kohn, "Effects of Surfactants and pH on Naltrexone (NTX) Permeation Across Buccal Mucosa" Int. J. Pharm. Jun. 15, 2011; 411(1-2): pp 92-97 ("Vishwas et al.") teaches the benefits of maintaining a pH of 6.8 to 8.2 for improved absorption of Naltrexone. For example, Vishwas et al states: "[s]lightly increasing the pH of NTX (naltrexone) from 6.8 to pH 7.5 and pH 8.5 increased permeation by a factor of 1.6 and 4.4 respectively." Id. at page 8, Conclusions, Section 4, Sentence 5. Naltrexone is an antagonist with a structure much like Naloxone but has a better affinity for the κ-opioid binding site. Vishwas et al. further teach the use of a particular surfactant to increase the buccal absorption of Naltrexone: "It was found that permeation of NTX across reconstituted human buccal mucosa produced an enhancement of 7.7 with the use of Brij 58." Id. at page 8, Conclusions, Section 4, Sentence 2. However, Vishwas et al. make no mention or suggestion of combining a surfactant with a pH buffer nor do they mention the use of two compartments to separate the buffer from the antagonist during the storage of the product. Nor do they teach how to have a storage-stable antagonist with a pH greater than 5 at the point of use.

Naloxone hydrochloride injection is formulated at a pH of approximately 4 to ensure chemical stability and physical stability below the equilibrium solubility of naloxone hydrochloride over the life of the product. The pKa of Naloxone is reported to be around 7.9 for the protonated amine. Based upon pH partition theory it may be expected that if the protonated unionized species has higher permeability through the oral mucosa, then maximal absorption could be expected at or around pH 7.9. However, sufficient absorption to elicit a therapeutic response could conceivably occur at pH greater than 5 and up to 12.

U.S. Pat. No. 6,110,926 teaches that aqueous solutions of Naloxone with buffers at pH 6.5 are subject to degradation and tests have shown that such solutions are in fact unstable, the naloxone content degrading over the course of a few days. This patent claims that the instability may explain the report by Loimar et al (The Lancet, May 5, 1990, pp. 1107-1108) that conjunctival naloxone does not provide a decision aid in determining opioid addiction. This patent and the Lancet paper, and their contents, are incorporated by reference into this specification as if fully set forth herein. It must also be noted that injectable naloxone is typically at a pH of 4 adjusted with hydrochloric acid presumably to avoid this instability.

Again, using naltrexone as an example, according to Vishwas et al., a pH of 6.5 is in the target pH range for optimizing the bioavailability (absorption) of the antagonist. However, neither the patents referenced above, nor Vishwas et al., teach how to both optimize the absorption of the antagonist and also protect the antagonist from pH-induced oxidation or hydrolysis during storage.

A rescue drug like naloxone cannot be administered orally to an unconscious patient who is unable to swallow an oral medication. Similar issues are seen with other rescue therapeutics. For example, a child in seizure cannot be instructed to swallow an oral medication. It may be difficult for a patient with severe migraine or post-operative pain to swallow a conventional oral dosage form. Similarly, patients with conditions like Parkinson's frequently have difficulty swallowing. Moreover, even if the patient can swallow an oral medication, it may simply take too long to reach efficacious blood levels.

However, even if Naloxone or like antagonists were given orally using conventional methods, they would be subject to first pass metabolism, and degradation and are consequently not bioavailable for blocking of the opioid receptors at the relevant receptor sites in the body. Smith K; Hopp M; Mundin G; Bond S; Bailey P; Woodward J; Bell D. Low Absolute Bioavailability of Oral Naloxone in Healthy Subjects, "Int. J. of Clinical Pharmacology and Therapeutics, 2012; 50 (5); pp 360-367" ("Smith et al.") and Manir A. Hussain; Bruce J. Aungst; Albert Kearney; Eli Shefter "Int. J. of Pharmaceutics, Vol. 36, Issues 2-3, May 1987, pp 127-130" ("Hussain et al.") teach low systemic bioavailability of naloxone and naltrexone due primarily to metabolization by the liver. Smith writes "The mean absolute bioavailability of naloxone from the orally administered PR tablets was very low, ranging from 0.9% for the 5 mg dose to 2% for 40, 80, and 120 mg doses based on AUCt." See Abstract Results, Sentence 1. Hussain writes "Both naloxone and naltrexone have been shown to be absorbed from the gastrointestinal tract. However, as a consequence of rapid clearance by the gut and/or liver, naloxone and naltrexone undergo extensive first-pass metabolism when given orally." See id., page 129, 2. The major metabolite is naloxone-3-glucuronide which is excreted in the urine. The foregoing references and their contents (including the references in preceding paragraphs) are incorporated into this patent application by reference and as if fully set forth herein.

Although the prior art has taught the use of buffers and permeation enhancers to increase the buccal absorption of an antagonist, no one has taught how to deliver a shelf life stable buffered solution of an opioid antagonist at the point of absorption and for this reason applicant believes that there is no buccal opioid antagonist product in the market for life saving and other medical purposes.

A major problem with Naloxone is that it is only stable and soluble in a low pH environment e.g., a pH of 5 or less and preferably at pH 4 or lower, but that it needs to be at a higher pH (e.g. a pH greater than 5 and up to a pH of 12) in order for maximum mucosal absorption of the drug. Therefore, there exists a need for a convenient method to administer an opioid antagonist like Naloxone that is stable over the shelf-life of the product but that can successfully deliver naloxone at high pH at the site of absorption. This invention teaches a way to administer a chemically stable (during storage) aqueous liquid or semisolid gel dosage form of an antagonist through a mucosal administration site, such as the oromucosal region (which encompasses buccal, sublingual and gingival areas), intranasal, vaginal or rectal. The invention shows how to achieve the contrasting requirements for stability and solubility at storage pH and adequate active absorption pH for pharmaceutical active agents in a single dosage unit encompassing two chambers.

SUMMARY OF THE INVENTION

One aspect of the invention relates to a kit for administering a mucosally absorbable composition to a human patient. The kit includes a first compartment comprising a first composition comprising a pharmaceutical active agent that is substantially lipid soluble and substantially water insoluble, in a substantially non-aqueous solution, and a second compartment comprising a second composition comprising a substantially aqueous solution. The first and second compartments maintain separation of the first and second compositions during storage, and allow for mixing of the first and second compositions to form a mixed mucosally absorbable composition for immediate mucosal administration to a human patient. In one embodiment, the second composition contains an acidic buffer and the mixed mucosally absorbable composition has an acidic pH; alternatively, the second composition contains a basic buffer and the mixed mucosally absorbable composition has a basic pH.

Mucosal administration to a human patient can be to at least one of the following mucosal administration sites, buccal, sublingual, intranasal, vaginal or rectal. Ocular administration is also contemplated.

Another aspect of the present invention relates to a kit for administering a mucosally absorbable composition to a human patient. The kit includes a first compartment comprising a first composition containing a substantially water-soluble pharmaceutical active agent in a solution together with one or more optional suitable pharmaceutical excipients, and a second compartment comprising a second composition with one or more optional suitable pharmaceutical excipients. At least one of the first and second compositions contains an effective amount of a crystallization inhibitor. The first and second compartments maintain separation of the first and second compositions during storage and allow for mixing of the first and second compositions to form a mucosally absorbable composition, which may comprise a gel, for immediate mucosal administration to a human patient. In one embodiment, the second composition in the second compartment is at an acidic pH and contains an acidic buffer and the mucosally absorbable composition has a pH<6; alternatively, the second composition in the second compartment is at a basic pH and contains an alkaline buffer and the mucosally absorbable composition has a pH>7.

In a preferred embodiment, when the mucosally absorbable composition is mucosally administered to a patient, it results in mean AUC more than 35% greater than the same dosage delivered orally. In a preferred embodiment, when the mucosally absorbable composition is mucosally administered to a patient, it results in a mean Tmax more than 25% faster than the same dosage delivered orally. In a preferred embodiment, when the mucosally absorbable composition is mucosally administered to a patient, it results in a mean Cmax more than 35% higher than the same dosage delivered orally. Other embodiments of the present invention may offer similarly improved performance at other mucosal sites, as compared with conventional drug formulations used at the reference sites.

Another aspect of the invention relates to a kit for mucosally administering a metastable supersaturated solution of a pharmaceutical active agent to a human patient. The kit includes a first compartment comprising a first composition comprising a pharmaceutical active agent in solution at or below equilibrium solubility, and a second composition comprising an acidic buffer. The first and second compartments maintain separation of the first and second compositions during storage, and allow for mixing of the first and second compositions to form a supersaturated solution above equilibrium solubility of the pharmaceutical active agent for immediate mucosal administration to a human patient. In one embodiment, the second composition comprises an acidic buffer and the supersaturated solution has an acidic pH.

Alternatively, the second composition comprises a basic buffer and the supersaturated solution has a basic pH.

BRIEF DESCRIPTION OF THE DRAWINGS

The accompanying drawings illustrate embodiments of the present invention.

FIGS. 1a, 1b, 2a, 3a, 3b, 4a and 4b show top or bottom views of a dual-chambered package in which labeled part 1 denotes its contents as one liquid of the present invention.

FIGS. 1a, 1b, 2a, 3a, 3b, 4a and 4b show top or bottom views of a dual-chambered package in which labeled part 2 denotes its contents as a second liquid of the present invention.

FIGS. 1c, 2b, 3c, 4c and 4d show side or edge views of a dual chambered packages which contains the two liquids of the present invention.

FIGS. 1b, 1c, 2a, 2b, 3a, 3b, 3c, 4a and 4c, labeled part 3 shows the separation barrier between the first and second chambers of the present invention.

In FIGS. 5 and 6, labeled part 1 shows a view of one chamber of a dual-chambered package which contains one liquid of the present invention.

In FIGS. 5 and 6, labeled part 2 shows a view of a second chamber of dual chambered package which contains a second liquid of the present invention.

In FIGS. 5 and 6, labeled part 3 shows a view of a syringe of the present invention, which shows a separation barrier between the first and second chambers. In FIG. 5, the syringe is a double barrel syringe wherein the two barrels are conjoined and each contains the two liquids of the invention separated from one another during storage. In FIG. 6, the syringe is a single barrel syringe with a frangible barrier between the contents of the upper and lower chambers.

FIG. 11 is a graph of Naloxone plasma concentration in a human study.

FIG. 12 is a graph of Nalbuphine plasma concentration in a human study.

DETAILED DESCRIPTION OF THE INVENTION

Figure 1A:
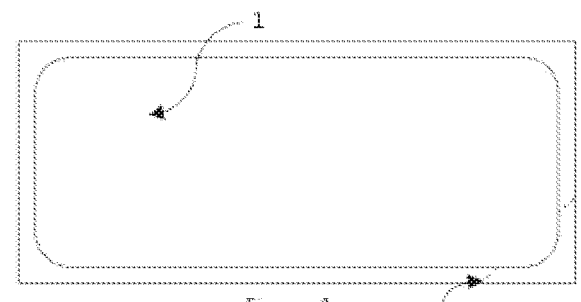
FIG. 1a, 1b, 1c, 1d, 2a, 2b, 2c, 3a, 3b, 3c and 4a, 4b, 4c and 4d show various views of four different embodiments of the device in pouch-type configurations.
Figure 1B:
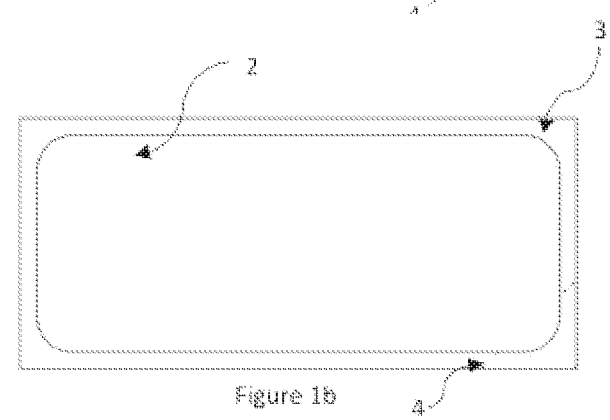
Figure 1C:
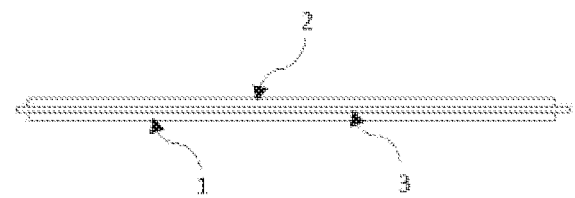
Figure 1D:
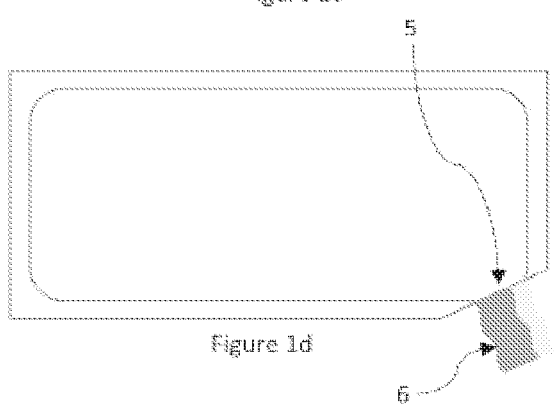
Figure 2A:
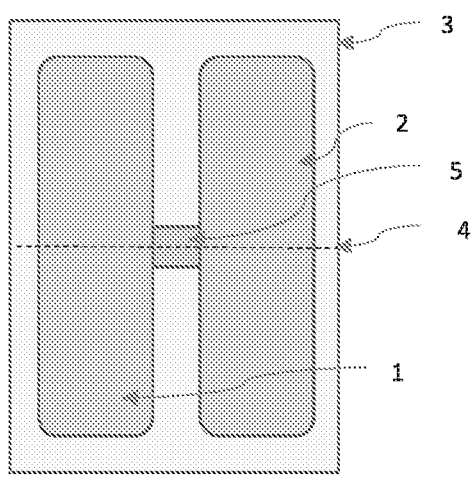
Figure 2C:
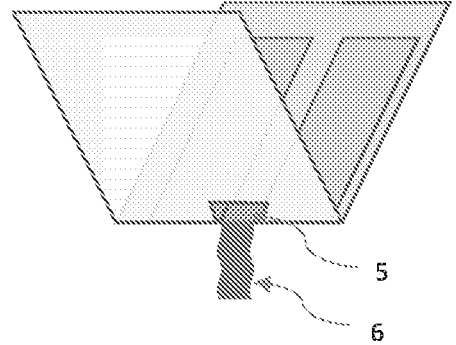
Figure 2B:
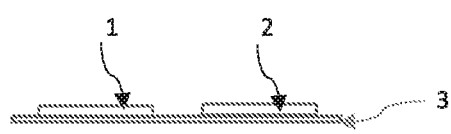

The drug naloxone is one example of a rescue therapy drug, i.e. used to rescue patients in opioid induced distress. While there is no single accepted definition of a "rescue therapy drug", the term is used herein to refer to treatment of: a life-threatening episode (e.g. opioid overdose), or an episode where severe, episodic symptoms are not effectively controlled or mitigated by the patient's "standard" drug regime (e.g. a severe asthma attack, or a prolonged or unexpected seizure), or episodic symptoms requiring immediate relief (e.g. migraine headache, post-surgical pain, menstrual pain, severe anxiety disorder/panic attack, angina, etc.). In addition to rescue therapeutics as defined herein, the invention may also be used as the primary treatment for any acute or chronic condition for which immediate relief is desired.

Oromucosal delivery is uncommonly used to deliver drugs for systemic pharmacologic effects because a drug viable for this route of administration must possess specific amenable attributes—the drug must be potent (low dose); and it must have ideal physicochemical properties of low molecular weight and high lipid solubility (high log P values) that allow a high rate of permeation through the oral mucosa. A few well-known examples of drugs successfully administered by the sublingual or buccal route are nitrates for angina; and fentanyl or buprenorphine for pain and addiction, nicotine, barbiturates and some psychoactives. It is particularly desirable to enhance the mucosal delivery of pharmaceutical actives for rescue use, i.e. a rescue therapy (the pharmaceutical agent being referred to as a rescue therapeutic). This is because it is one of three non-injectable mucosal routes (nasal, rectal and oromucosal) available in subjects. Of these, the oromucosal route is preferable and even more so in self-administered rescue applications. However, despite the potential advantages of this route of administration it is rarely employed in rescue therapeutics because the residence time at the oromucosal route is shorter and drug must rapidly reach the required therapeutic levels in the blood to effect the rescue—this is a particularly tall order for an already formidable oromucosal barrier to absorption for most drugs.

The ability to provide effective oromucosal delivery creates the opportunity to provide rapid relief to patients particularly where the historic lack of oromucosal treatment options presents unmet medical needs. Non limitative examples include oromucosally absorbable pharmaceutically actives like analgesics for relief of migraine headache, post-surgical pain, menstrual pain, labor pain; anxiolytics for severe anxiety disorder/panic attack; bronchodilators for anaphylactic shock and acute respiratory distress; anti-allergenics for treatment of hypersensitivity and allergic reactions, arterial dilators for angina; rescue anti-emetics for post-operative nausea, motion sickness and vertigo; rescue anti-hypertensives for emergency treatment of high blood pressure; opioid and benzodiazepine antagonists for drug overdose reversal and anticholinergics as antidote drugs.

In many cases, with the present invention, it should be possible to deliver rescue therapy and other drugs oromucosally more reliably than can be achieved through intranasal delivery.

In many cases, with the present invention, drugs can be delivered more rapidly and effectively intranasally or to other mucosal administration sites (e.g. rectal, vaginal) than with traditional formulations.

In many cases, with the present invention, it should be possible to deliver rescue therapy and other drugs oromucosally more conveniently than can be achieved through rectal delivery.

In many cases, with the present invention, it should be possible to deliver rescue therapeutics and other drugs by self-administration by a conscious patient or by a caregiver to an unconscious patient.

In many cases, with the present invention, it should be possible to successfully deliver rescue therapies and other drugs mucosally, thereby avoiding, or at least reducing, the need for injectables and effecting faster relief than is available through GI administration of conventional dosage forms such as tablets or capsules, or traditional solid oromucosal dosage forms (e.g. orally dissolving tablets, orally soluble films, sublingual sprays, etc).

One object of certain embodiments of the present invention is to provide a drug composition and delivery device for the mucosal administration of a pharmaceutically active agent in an oral liquid or gel that is stable and solubilized during the shelf life of the product.

Another object of certain embodiments of the present invention is to provide a rapidly buffered pharmaceutically active agent, including without limitation an antagonist, and to rapidly deliver the therapeutically effective blood levels of said pharmaceutically effective agent.

In certain embodiments, the present invention provides a pharmaceutically active agent in a transiently stable solution, where the solution is intended to maximize mucosal delivery.

In certain embodiments, the present invention provides a pharmaceutically active agent in a micellar solution for mucosal delivery.

In certain embodiments, the present invention provides a pharmaceutically active agent in a multi-lamellar liquid crystal phase for mucosal delivery.

In certain embodiments, the present invention provides a pharmaceutically active agent in a microemulsion for mucosal delivery.

In certain embodiments, the present invention provides a pharmaceutically active agent in an optically isotropic microemulsion for mucosal delivery.

In certain embodiments, the present invention provides a pharmaceutically active agent in a nanoemulsion for mucosal delivery.

In certain embodiments, the present invention provides a pharmaceutically active agent in an isotropic nanoemulsion for mucosal delivery.

In certain embodiments, the present invention provides a pharmaceutically active agent in an emulsion for mucosal delivery.

In certain embodiments, the present invention provides a pharmaceutically active agent in a gel for mucosal delivery. Said gel (as well as non-gel embodiments) may optionally be mucoadhesive, and may optionally comprise a mucoadhesive agent.

In certain embodiments, the present invention provides a pharmaceutically active agent in a super saturated solution for mucosal delivery. Super saturation may be effected, without limitation, by pH change or by dilution/solvent-change methods. In certain embodiments, the present invention provides a super saturated solution ex vivo, prior to administration to the mucosa.

In certain embodiments, the pharmaceutically active agent is maintained in solution in a compartment with a pH that is optimized for chemical stability of the drug to prevent oxidation, hydrolysis or other degradation of the pharmaceutically active agent.

In certain embodiments, the pharmaceutically active agent is maintained in a compartment with a pH that is optimized for physical stability by maintaining the pharmaceutically active agent in solution at or below equilibrium solubility.

As defined herein, a drug may be described as substantially insoluble in water which means the drug would be insoluble, practically insoluble, very slightly soluble or slightly soluble as defined in the United States Pharmacopoeia (USP). The drug may be substantially soluble in water which means it is very soluble, freely soluble, soluble or sparingly soluble as defined in the USP. Similarly, a drug maybe substantially lipid soluble where the drug is soluble in a combination of liquids that consist substantially of lipidic or amphiphilic compounds such as a surfactants and non-polar solvents but may also contain some water (i.e. a substantially non-aqueous solution). On the other hand, a substantially aqueous solution means that the solution consists predominantly of water and other polar co-solvents such as PEG, PG and ethanol but may also contain amphiphilic surfactants. A surfactant as defined herein is an organic compound with both hydrophilic (water-soluble) and lipophilic (lipid soluble) groups thereby possessing amphiphilic characteristics that enable the formation of micelles, emulsions and liquid crystal structures when combined with lipids and water. Surfactants may have a range of hydrophilic lipophilic balance (HLB) values. Emulsions are multi-phasic liquid, semi-solid or gel systems formed when one liquid component is dispersed as distinct organized spherical or non-spherical structures within a continuous phase of another liquid. The dispersed phase may spontaneously emulsify in the continuous phase as nanometer-sized, micron-sized or millimeter sized droplets or other ordered multi-lamellar structures.

Similarly, in certain embodiments, the present invention delivers to the mucosa predominantly the protonated form of the pharmaceutically active agent at a suitable pH, or range of pH, based on the pKa of the drug. Pharmaceutically active compounds may either be bases or acids. Generally speaking, acidic drugs tend to be more soluble at basic pH and basic drugs would be more soluble at acidic pH. Basic drugs include, inter alia, aliphatic amines, anilines, basic amides, amidines, guanidines and heterocyclic nitrogen atoms. Drugs with acidic groups (acidic drugs) include, inter alia, carboxylates, phenols, sulfonamides and also heterocyclic nitrogen atoms and less commonly phosphates, tetrazoles, thiols, alcohols carbamates, hydrazides, imides and sulfates.

For acidic drugs with physiologically relevant ionizable groups, a pH between 2 and 5 at half to one pH unit below the pKa of the drug so that a majority of the drug would exist as the unionized/protonated species. Similarly, for a basic drug a pH between 7 and 11 at a value half unit or greater above the pKa to predominantly present the unionized form of the drug. In certain embodiments, the present invention employs surfactants, buffering agents, polymeric crystallization inhibitors, polymeric gelling agents, anti-oxidants, chelating agents and other stabilization agents, mucoadhesive agents, sweeteners, absorption enhancers, lipidic excipients, alcoholic or poly-alcoholic co-solvents, pH-indicators, and multiple compartments to separate incompatible excipients (e.g. separate a pH buffer from the pharmaceutically active agent).

Another object of certain embodiments of the present invention is to provide a portable, non-injectable mucosal drug delivery system for drugs including for rescue therapeutics which can be administered in urgent medical circumstances. A non-limitative example is where a patient suffers from an opioid overdose but may not be located in proximity to a medical facility.

Currently there exists no method of oral or oromucosal delivery of emergency opioid antagonist. The challenge with oral delivery of opioid antagonist is with the rapid first pass metabolism of the antagonist and also that the patient in acute overdose is often unconscious. The most common treatment of overdose involves injection of the antagonist in an emergency treatment setting. Even if oral naloxone could be delivered to a patient experiencing opioid overdose, the amount of naloxone absorbed would be insufficient to reverse the overdose. Hussain et al. reports a 1% bioavailability in mice for an orally delivered Naloxone. Smith et al. also report the mean absolute bioavailability of oral Naloxone in healthy subjects at less than or equal to 2% at doses ranging from 5 mg to 120 mg. Still further, it is virtually assured that the time to reach efficacious blood levels from conventional oral administration would be unacceptably long. Oral administration of Naloxone for emergency treatment of opioid overdose is therefore not feasible.

Similarly, there are no approved oromucosal products for many rescue needs. For example, there is no available oromucosal treatment for epilepsy, migraine or anxiety attacks. Similarly there is a need for better performing mucosal drug products generally, with improved PK performance. For example, drugs may be available only in parenteral form because of poor bioavailability when administered orally. In other cases, mucosally absorbable versions may exist but better absorption performance is desirable.

As noted above, because of rapid first pass elimination of an antagonist, non-peroral administration of the antagonist is required. Parenteral administration is effective but is invasive and requires trained personnel to administer the drug to an unresponsive overdosed subject. Oromucosal absorption circumvents these problems with oral and parenteral administration because it is non-invasive and also avoids first pass metabolism of the active as it is delivered directly to the circulatory system. Further improvement of drug absorption is expected in the presence of permeation enhancer(s) or if the pH of the absorption environment is at a pH of 5 or greater as reported by Vishwas et al in the example of naltrexone. However, what Vishwas et al. fails to teach is the combination of a permeation enhancer in the presence of a buffer with a pH greater than 5. Vishwas et al. also fails to teach how to achieve the use of a buffer of pH of 5 or greater at the 'point of use/site of absorption' without loss of stability of the antagonist. For example, it is well known that at pH>6, morphine degrades through two oxidation pathways and in both cases, the oxidation rate increases with deprotonation of each functional group. See also U.S. Pat. No. 6,110,926 which, together with its contents is incorporated into this specification by reference as if fully set forth herein. In contrast, the present invention teaches how to achieve a pH greater than 5 at the point of use and site of administration, for maximal buccal absorption of the opioid antagonist while at the same time maintaining the antagonist in a lower pH environment prior to use to achieve a chemically stable product that can be stored at room temperature.

In a preferred embodiment, the composition and drug delivery system of the present invention comprises a mucosally absorbable liquid composition for administration to a human patient of pharmaceutically active agent, (e.g. an opioid antagonist) comprising one composition containing pharmaceutical active in solution with other suitable pharmaceutical excipients in a distinct compartment of a multi-compartment device or container comprising two or more chambers; a second composition at a pH greater than 5 containing a buffer or alkaline components with other suitable pharmaceutical excipients in a second distinct compartment of the same multi-compartment device, and a device or system which maintains separation of the first and second liquids during storage and allows for mixing of the two liquids to form a mucosally absorbable composition, which may be of gel-like or cream-like consistency at the point of use to prevent flow of the product away from administration site.

In accordance with the purposes of the present invention, as embodied and broadly described herein, the present invention includes the composition, device and method that will allow for the delivery of a transiently stable composition to a human subjects' oromucosal region, or other mucosal site.

Preferably, this is achieved by the creation of an aqueous opioid antagonist (or other pharmaceutically active agent) composition in the pH range of optimal stability and solubility that is housed by itself in one chamber of a multi-chambered package. In the other chamber of the package, a buffer of pH greater than 5 is housed. Optimal stability means that the drug retains 90% of its activity for an 18-24 month shelf life. There exists a barrier that separates the chambers, and maintains total separation of the compositions. During use, the buffer composition and the antagonist composition are mixed together either just before being placed in the patient's mouth or within the patient's mouth, thereby delivering a buffered oromucosally absorbable mixed composition at pH greater than 5 and preferably greater than the pKa of the antagonist to maximize absorption by presenting the unionized species at the point of administration. The composition may be delivered to other mucosal sites. The two compositions are mixed to create the final mixed composition within which the drug may no longer be storage stable (transiently stable), however, the mixed composition is intended to be instantly used (oromucosally delivered) within a few minutes of mixing (preferably within one minute, more preferably within ten seconds) and not stored for future use.

This mixed composition may be expected to result predominantly in the protonated species of the drug that is typically less soluble in aqueous media at a pH greater than the pKa of the drug. The drug concentration in the mixed composition may now be significantly higher than the saturation solubility of the drug causing the transient existence of a metastable super-saturated solution. This metastable state is a relatively long-lived state of precarious stability but not a permanent equilibrium state. It will eventually convert via phase transition to the more stable lower energy state of a crystallized solid. Use of appropriate crystallization inhibitors at suitable (effective) concentrations is important in such embodiments, to effect and maintain the transient metastable state of the supersaturated solution long enough to ensure rapid absorption in the oromucosal cavity or other mucosal administration site. Preferably, the transiently metastable super saturated solution lasts more than five minutes, more preferably more than ten minutes, most preferably more than fifteen minutes. The transiently stable super saturated solution is preferably a gel or solution substantially free of a precipitated solid phase of pharmaceutically active agent. Preferably, the transiently stable super saturated solution is a clear gel.

A fraction of the oromucosally administered drug may be absorbed quickly in this way while the remaining fraction of drug may be expectorated or otherwise intentionally or inadvertently swallowed to subsequently be absorbed via the typical (and slower) oral route to maintain blood levels. The rapidly absorbed oromucosal fraction may thus serve as an initial loading dose followed by slower and more sustained absorption from the gastro-intestinal tract.

One basic drug (as free base or as a salt) in a chamber is present as a solution in water (or water plus alcohol or other co-solvents). The solution within this chamber may also have polymer/s (or other gelling agents) to provide a viscous liquid or semi-solid or gel-like consistency. It may also have an acidic component or a buffer pair to bring the pH to the acidic region of pH 6 or lower to improve drug stability and solubility (similarly, basic components or buffer pairs may be used to bring the pH to the basic region where the pharmaceutically active agent is more stable at basic pH). It may also have colorant, permeation enhancer, an antioxidant, a pH-indicating dye, and/or other components as described in this specification.

The other chamber contains a base or buffer pair in solution (or acid or buffer pair where the rescue drug is better absorbed at an acidic pH). Generally, the other chamber has a stronger acid or base or buffer pair capacity to control the pH of the combined solution (overcoming the acid or base or buffer pair of the chamber containing the pharmaceutically active agent) and maintain such pH at or above the pKa (for basic pharmaceutical actives), or at a pH at or below the pKa (for acidic pharmaceutical active agents) at the site of mucosal administration. Preferably, such pH at the mucosal administration site is maintained >5 minutes, more preferably >10 minutes, and most preferably >15 minutes.

In the case of naloxone hydrochloride, this would typically be a higher pH buffer well above pH 5 that is included for the purpose of increasing the combined solution/gel to a pH at or above the pKa of the drug and maintain the pH greater than the pKa of the drug at the site of absorption to maximize absorption. This chamber may also contain a polymer to make it a viscous liquid or gel, and it may contain dye, permeation enhancer and other pharmaceutical excipients, but an antioxidant is optional here because there is no drug in this chamber.

In another embodiment typifying a reverse approach, an acidic drug (as free acid or as a salt) in a chamber is present as a solution in water (or water plus alcohol or other co-solvents). The solution within this chamber may also have polymer/s to provide a viscous liquid or semi-solid or gel-like consistency. It may be at neutral pH or have a basic component or a buffer pair to bring the pH to the basic region above pH 7 to improve drug stability and/or solubility. It may also have colorant, permeation enhancer, an antioxidant, a pH-indicating dye, and/or other components as described in this specification. The other chamber contains an acid or acidic buffer pair in solution (where the rescue drug is better absorbed at an acidic pH). In the case of an acidic drug like ketorolac, this would typically be a lower pH citrate or other buffer below pH 4 that is included for the purpose of decreasing the combined solution/gel to a pH below 4 and maintain the pH at or below the pKa of the drug at the site of absorption to maximize absorption. In many embodiments, one or both chambers will comprise a crystallization inhibitor.

Some embodiments of this invention would consist of a kit in which the compositions in each of the two compartments are single phase compositions such as solutions. However, in other embodiments one or both of the individual compositions within each compartment of the kit may also contain another dispersed phase. Each individual liquid composition may either be a single phase solution or a multi-phasic emulsion. When the two compositions are combined prior to administration the resulting mucosally absorbable composition may be a single phase solution as a hydrogel or a multi-phasic emulsion as a cream.

The system of the present invention may be employed with multi-active ingredient combination products, i.e. more than one pharmaceutically active agents. In such cases, the multi-chambered architecture may be particularly valuable to ensure stability of each pharmaceutically active agents, by segregating such agents in different environments (akin to other embodiments of the present invention). Different environments may be particularly desirable to maintain product stability.

The pharmaceutically active agents used in the system of the present invention may be free bases and any suitable salt thereof as well as free acids and any suitable salts thereof. The pharmaceutically active agents may comprise prodrugs.

The two-chambered constructions disclosed herein provide some of the possible embodiments of the present invention. For example, other embodiments, as would be recognized by those of ordinary skill in the art, may contain higher multiples of compartments or chambers, and varying constructions that would achieve the objects of the present invention.

In accordance with the above objects and others, the present invention is directed in part to a mucosally absorbable liquid composition for administration to a human patient, comprising one liquid containing an ionizable pharmaceutically active agent together with one or more optional suitable pharmaceutical excipients in a first compartment at a pH≤6; and a second liquid at pH≥6 containing a buffer or alkaline components together with one or more optional suitable pharmaceutical excipients in a second distinct compartment; wherein the first and second compartments maintain separation of the first and second liquids during storage such that the pH-sensitive drug is maintained in solution at a storage-stable pH and allow for mixing of the first and second liquids to form a mucosally absorbable composition having a pH≥6 for immediate mucosal administration to a human patient. In certain preferred embodiments, the pH-sensitive pharmaceutically active agent is an opioid antagonist (e.g., naloxone). In certain preferred embodiments, after mixing the contents of the first and second chamber, the pH of the resultant composition is greater than 6, e.g., from about 6 to about 12. In certain preferred embodiments, after mixing the contents of the first and second chamber, the pH of the resultant composition is from about 6.5 to about 9.5. In other preferred embodiments, after mixing the contents of the first and second chamber, the pH of the resultant composition is from about 7.5 to about 9. In other preferred embodiments, after mixing the contents of the first and second chamber, the pH of the resultant composition is 6, 6.5, 7, 7.5, 8, 8.5, 9, 9.5, 10, 10.5, 11, 11.5 or 12. In the most preferred embodiment, after mixing the contents of the first and second chamber, the pH of the resultant composition is at or above the pKa of the drug. In further preferred embodiments, the pH of the liquid contained in the first compartment prior to mixing is from about 1 to about 6. In further preferred embodiments, the pH of the liquid contained in the first compartment prior to mixing is 1, 1.5, 2, 2.5, 3, 3.5, 4, 4.5, 5, 5.5, 5.6, 5.7 5.8, 5.9 or 6. In certain preferred embodiments, the pH of the liquid contained in the first compartment prior to mixing is from about 3 to about 6.

In accordance with the above objects and others, the present invention is directed in part to a mucosally absorbable liquid composition for administration to a human patient, comprising one composition containing an ionizable acidic pharmaceutical active agent in solution together with one or more optional suitable pharmaceutical excipients in a first compartment at a pH>6; and a second composition at pH≤6 containing a buffer or acidic components together with one or more optional suitable pharmaceutical excipients in a second distinct compartment; wherein the first and second compartments maintain separation of the first and second compositions during storage such that the pharmaceutically active agent is maintained in solution at a storage-stable pH and allow for mixing of the first and second compositions to form a mucosally absorbable composition having a pH≤6 for immediate oromucosal or mucosal administration to a human patient. In certain embodiments, the drug may be pH-sensitive which means that the pharmaceutical active is chemically unstable over the shelf life of the active i.e. does not maintain at least 90% of its biological activity or analytical identity and/or a pH wherein the active has insufficient equilibrium solubility to keep the drug in solution over its shelf life. In certain preferred embodiments, the pharmaceutically active agent is a rescue therapy or other drug best absorbed at an acidic pH. In certain preferred embodiments, after mixing the contents of the first and second chamber, the pH of the resultant composition is from about 6 to about 1. In certain preferred embodiments, after mixing the contents of the first and second chamber, the pH of the resultant composition is from about 3 to about 6, preferably less than 5.5. In other preferred embodiments, after mixing the contents of the first and second chamber, the pH of the resultant composition is from about 3.5 to about 5.5. In other preferred embodiments, after mixing the contents of the first and second chamber, the pH of the resultant composition is 1, 1.5. 2. 2.5, 3, 3.5, 4, 4.5, 5, or 5.5. In the most preferred embodiment, after mixing the contents of the first and second chamber, the pH of the resultant composition is at or below the pKa of the drug. In further preferred embodiments, the pH of the liquid contained in the first compartment prior to mixing is from about 6 to about 12. In further preferred embodiments, the pH of the liquid contained in the first compartment prior to mixing is 6, 6.5, 7, 7.5, 8, 8.5, 9, 9.5, 10, 10.5, 11, 11.5, 12, 12.5, or 14. In certain preferred embodiments, the pH of the liquid contained in the first compartment prior to mixing is from about 6.5 to about 11.

The present invention is further directed to a method of treating a human patient in need of treatment with a pharmaceutically active agent, comprising administering to a human patient the mucosally absorbable liquid composition comprising the steps of opening the first and second compartment; causing the first and second liquids to mix; and delivering the resultant mixture to a mucosal surface of a human patient. The contents of the compartments, are preferably delivered to the buccal, sublingual or gingival areas of the oral cavity.

The present invention is further directed to a method of treating a human patient in need of treatment with a pharmaceutically active agent that is only stable and soluble in a low (or high) pH environment, comprising administering to a human patient the mucosally absorbable liquid composition comprising the steps of opening the first and second compartment; causing the first and second liquids to mix; and delivering the resultant mixture to the intended mucosal surface.

Generally, the present invention will deliver a total combined liquid (preferably a gel) dose of less than 2 grams, more preferably less than 1.5 grams and most preferably less than 1 gram. Limited amounts are important for comfortable delivery to intended oromucosal sites, e.g. buccal cavity, sublingual area, etc. Limited amounts are also important to maintain relatively high levels of concentration of the pharmaceutically active agent. Preferably, the concentration of the pharmaceutically active agent comprising >5 mg/g of the delivered gel formulation, more preferably >20 mg/g of the delivered gel formulation, most preferably >40 mg/g of the delivered gel formulation.

The schematic representations provided in the FIGS. 1 through 6 provide descriptions of some of the possible embodiments of the invention. During the manufacturing process the fluid containing the active drug component is deposited into one compartment labeled 1 and a buffer greater than pH 6 is deposited into a second compartment labeled part 2 (where an acidic drug is better absorbed at an acidic pH, the second compartment may be filled with an acidic buffer solution with pH less than 6). Labeled part 3 represents the separation barrier between the two compartments labeled 1 and 2. In FIG. 1a or 1b, tearing along labeled part 4 causes both chambers to be opened and the compositions to exit from the pouch (labeled part 5 in FIG. 1d) and allow the contents (labeled part 6) to exit and be mixed at the point of use. FIGS. 2a and 2c show that the package folded along the axis part labeled 4 breaches a frangible seal labeled part 5 thereby allowing the two compositions to mix and exit the device as shown in labeled part 6. In FIGS. 3a and 3b, each of the two chambers has a frangible seal shown by labeled part 4 which may be breached by squeezing the two chambers between the fingers prior to use causing the contents of each chamber to enter a mixing zone (labeled part 5) with final exit of the mix (labeled part 6) through nozzle (labeled part 7). FIG. 4a shows how a first frangible seal (labeled part 4a) may be breached by squeezing the pouch such that contents of chamber labeled 1 and chamber labeled 2 are mixed together as shown in FIG. 4b prior to exiting from the pouch via nozzle labeled 7 after a second frangible seal (labeled 4b) is breached with further squeezing of the pouch to enable exit of the mixed composition (labeled part 6). The contents of compartment 1 and 2 are then brought together during use by various means as shown in the FIGS. 1d, 2c, 3c and 4b.

Figure 3A:
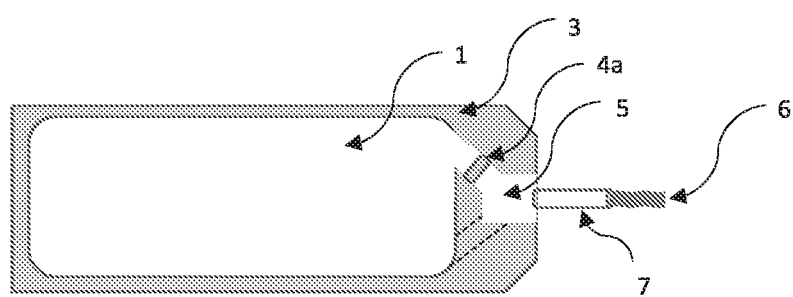
Figure 3B:
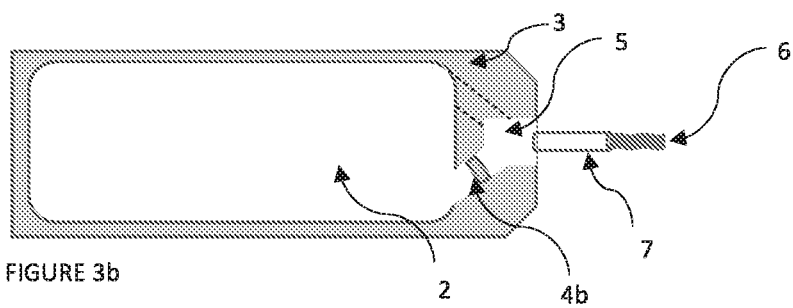
Figure 3C:
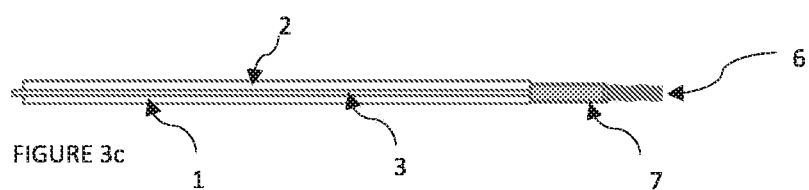
Figure 4A:
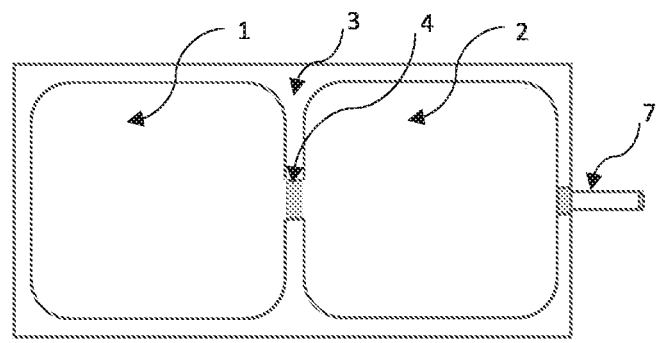
Figure 4C:
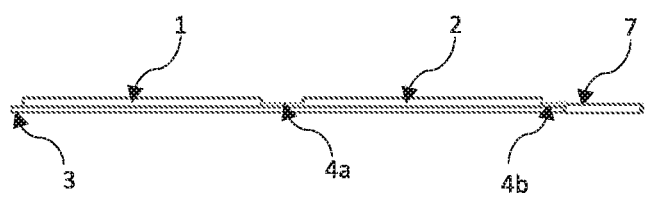
Figure 4B:
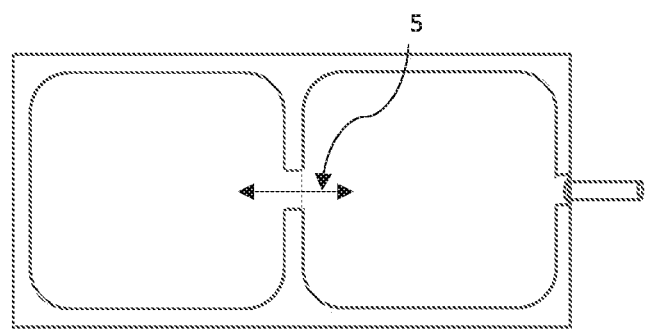
Figure 4D:

As an example, in FIGS. 3a, 3b, 3c, during use, the pouch is squeezed between fingers thereby breaching the frangible seals and allowing the two liquid streams to flow into a mixing zone prior to expulsion of the combined liquids from the dual compartment package. An opioid antagonist is instantly buffered to a pH greater than 5 at the point of use, for example, in the patient's buccal, sublingual or gingival regions. Other pharmaceutically active agents may be buffered to acidic or basic pH, as desired.

Figure 5:
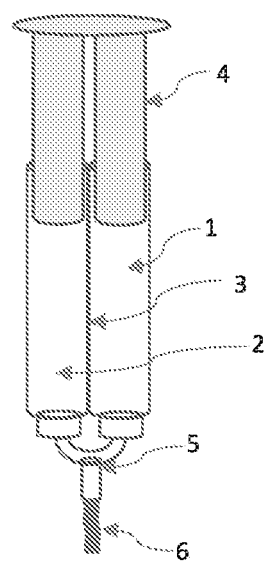
FIGS. 5 and 6 show two different embodiments of the device in a syringe configuration.
Figure 6:
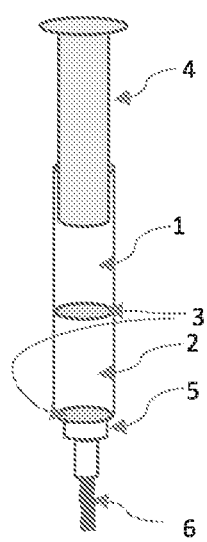
Figure 7:
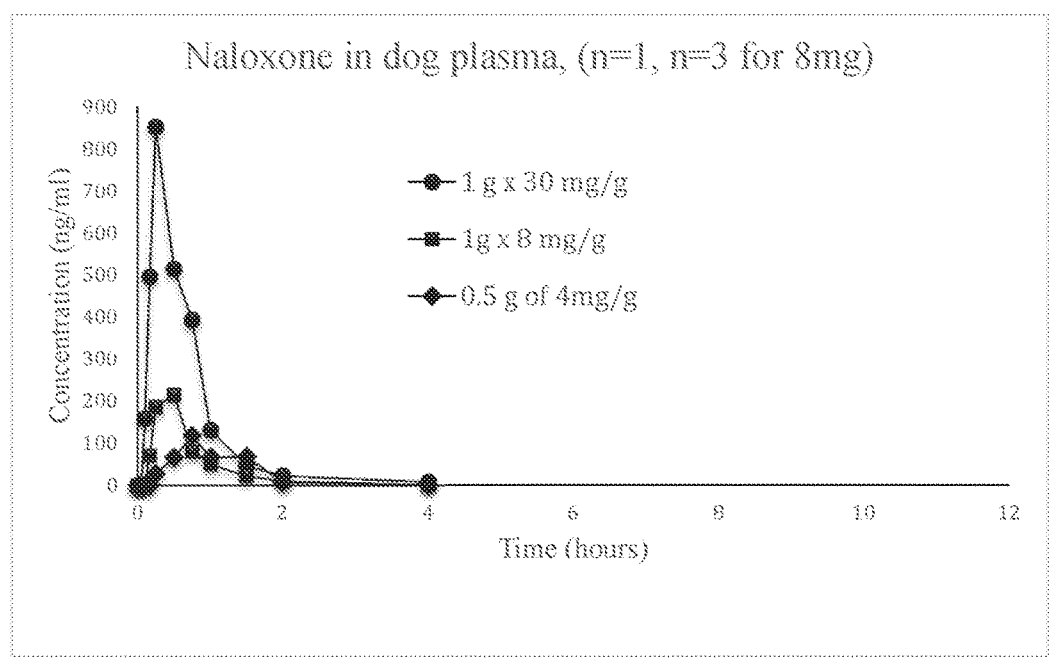
FIG. 7 is a graph of Naloxone plasma levels for test animals from an animal study.
Figure 8:
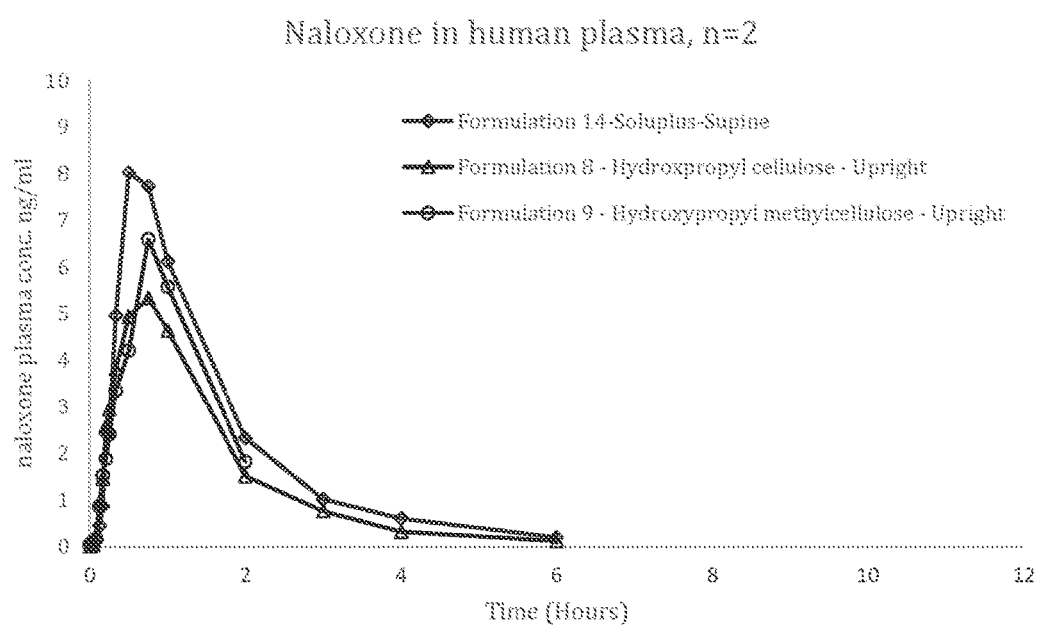
FIG. 8 is a graph of Naloxone plasma levels in a human study.

As shown in FIGS. 5 and 6, syringe designs may also be used to achieve the same objective. Similarly, in FIG. 5, when plunger (labeled part 4) is depressed, the contents of the both chambers, 1 and 2, pass through a mixing zone/nozzle (labeled part 5) to exit as a combined liquid mixture (labeled part 6). In FIG. 6, when plunger (labeled part 4) is depressed, the contents of chamber 1 are forced through contents of chamber 2 and then exit through a mixing zone/nozzle (labeled part 5) to exit as a combined liquid mixture (labeled part 6). The mixing zones (labeled part 5) of FIGS. 5 and 6 may take the form of a barrel, nozzle or tip that may contain in-line mixing configurations using screw threads or other designs known in the art. The plunger may be operated by hand, by spring, pneumatic pressure or other automatic system.

The current depiction of the pouch type embodiments in FIGS. 1a, 1b, 1c, 1d, 2a, 2b, 2c, 3a, 3b, 3c and 4a, 4b, 4c and 4d are composed of flexible aluminum laminate foil; however, plastic, paper, metal, glass or any reasonably useful material is within the scope of the present invention. The syringe type embodiments are composed of polypropylene or polyethylene; however, glass, metal or any other suitable polymeric resin or other useful material is within the scope of the invention. In sum, the package or containers can be any design that can house two flowable compositions and maintain a barrier between the two compositions and allows the two compositions to mix during use at or before the site of administration. The compositions may be slightly viscous liquids or very viscous liquids or shear-thinning liquids or shear-thinning gels or shear-thinning creams. A flowable liquid-like consistency is preferred for each of the individual liquid compositions so that it flows easily out of the syringe and mixes readily together. However, a less flowable liquid or a gel-like consistency is preferred after the compositions have combined and mixed in order to reduce flowability and reduce salivary dilution at the site of administration in the mouth. This would also allow the gel to stay in place in the oromucosal (or vaginal or rectal) cavity and impede involuntary or inadvertent swallowing of the composition (or other evacuation by bodily fluids).

The mucosally absorbable composition can be of a water viscosity but preferably a viscosity of 25 cps or more is employed, and more preferably, an aqueous gel of 100 cps and above is employed, and most preferably a gel of 1500 cps and above. Ideally, the viscosities of the liquids in compartments 1 and 2 should be such that efficient mixing of the liquids can be achieved.

As an example, the antagonist composition is housed in compartment 1 of FIG. 1-6. The aqueous buffer composition of pH greater than 5 is housed in the second compartment, 2 of FIG. 1-6, of the two-chambered package and the composition can be like water viscosity but preferably a viscosity of 2000 cps or less and more preferably an aqueous gel and can contain a water soluble polymer. The viscosity of the mixed composition (labeled part 6) of FIG. 1-6 should be such that the liquids or gels from both compartments, 1 and 2 are readily miscible. Both the buffer and pharmaceutical active containing composition can contain a permeation enhancer. Skilled artisans will appreciate, based on the disclosure herein, that acidic buffer compositions may also be employed for acid drugs.

The two chambered delivery device is arranged such that a barrier exists (FIGS. 1-6) between the two chambers in such a way that no contact between the two compositions in the two chamber occurs during storage. It is this barrier that allows for the separation of the stable aqueous antagonist solution or gel from the higher pH solution to maintain drug stability until the point of use. Skilled artisans will understand that the solution may comprise any pharmaceutically active agent, and that the pH may be acidic or basic to facilitate drug stability and solubility until the point of use in the oral cavity or other mucosal surface.

During use the two compositions (antagonist and buffer) in compartments 1 and 2 of FIGS. 1-6, are mixed either through turbulent mixing during expulsion from the package, or at the point of use. In this way, a buffer of greater than 5 is present during the actual use of the product but does not subject the antagonist to undue storage instability or insolubility by coming in direct contact with the buffer at pH greater than 5. Skilled artisans will understand that the solution may comprise any pharmaceutically active agent, and that the buffers may be inverted (acidic) as desired.

A commercially available double barrel syringe similar to that shown in FIG. 5 was a commercially obtained along with a mixing tip nozzle commonly used in dental resin mixing applications. This mixing tip nozzle contained an embedded static screw type mixer. This system was used for animal and human studies and also functions in a similar manner to the devices shown in FIG. 1-6. The two conjoined barrels of the syringe house the active gel and buffer gel separate from each other and are combined together as they are ejected through a static mixing nozzle which was attached prior to administration.

Applicant notes that in certain embodiments, it may be desirable to employ different fill volumes from the two (or more) chambers. As a non-limitative example, the first pharmaceutical active containing chamber may be larger than the second buffer containing chamber (or the inverse may be true). Different fill volumes may be achieved in a number of ways. A non-limitative example is to employ different chamber sizes (e.g. chambers with different diameters). Different fill volumes may be employed as a strategy to minimize total volume of the mixed composition. Minimizing fill volume may be particularly desirable where the intended mucosal site of administration is not (or may be perceived to not be) amenable to larger administered volumes. For example, the buccal or intranasal administration sites may accommodate smaller delivered volumes than rectal or vaginal sites. In other cases, consumer preference simply may favor smaller administered volumes.

Smaller volumes may also help to speed evacuation time from the delivery device. As a general matter (apart from volume), it is desirable that the composition can be rapidly expelled from the device, preferably within three seconds, more preferably within two seconds, and most preferably within one second.

Of course, if the volume of the buffer chamber is reduced, careful consideration must be afforded to the effects on the mixed composition, including the effects on various attributes including inter alia transient stability of the pharmaceutical active. There is an optimal combination in terms of formulating lower aggregate mixed volumes, while not unduly reducing the duration of transient stability. It is an aim of certain embodiments of the present invention to minimize aggregate mixed volumes, while maintaining a desired duration of transient stability. Because effective drug absorption is the primary goal for most embodiments, the formulation can be optimized including the minimization of optimal mixing volumes, based on the desired duration of transient stability, as well as buffer capacity that is desired for various administration sites (and their relative flows of bodily secretions which must be accounted for in thinking about pH for the intended duration of absorption). Where this aim implies different fill volumes, the device must accommodate such different fill volumes.

The antagonist is most stable at pH 5 or less; therefore, suitable acidic components or buffer pairs are used to keep the antagonist at lower pH in the composition. The preferable pH for this composition is less than 5, more preferably less than 4, and most preferably 3 or less. During use of the product the antagonist's low pH buffer's capacity will be overcome by the mixing of the antagonist composition with greater than pH 5 buffer composition, which is contained in the second compartment. The final pH at the point of use will be greater than 5. Skilled artisans will appreciate that different pharmaceutically active agents may be used, buffers may be changed, such that the final pH at the point of use is acidic or basic.

Further stability of the antagonist can be maintained during storage by the use of antioxidants and/or metal chelators and/or polyols. Either compartment can contain a pH indicator or other mixing indicators for observation and confirmation of mixing during use of the product.

Further stability of the pharmaceutically active agent can be maintained during storage by the use of a low pH buffer (or high pH buffer, as appropriate for a given pharmaceutically active agent), preferably 3 or less in the case of an antagonist, with one or more of the following: antioxidants (e.g. 0.0001-10%), metal chelators (e.g. 0.0001-2%) and polyols (e.g. 0.0001-15%).

Both liquid compositions may contain one or more of the following: pH indicators (e.g. 0.001-5%), sweeteners (e.g. 0.01-10%), flavorings (e.g. 0.01-2%), polymers (e.g. 0.01-80%), permeation enhancers (e.g. 0.01-20%), crystallization inhibitors (e.g. 0.01-20%) and other suitable pharmaceutically acceptable ingredients (e.g. 0.001-80%). Effective amounts of each such agent may be employed.

Naloxone injections are reported to be stable at pH 2.5-5. Following dilution in 5% dextrose or 0.9% sodium chloride injection to a concentration of 0.004 mg/mL (4 ug/mL), naloxone hydrochloride solutions are apparently stable for 24 hours; after 24 hours, any unused solution should be discarded. The injections also may contain methylparaben and propylparaben as preservatives. (American Society of Health System Pharmacists; AHFS Drug Information 2009. Bethesda, Md. (2009), p. 2254, hereby incorporated by reference). Naloxone injection may be diluted for intravenous infusion in normal saline or 5% dextrose solutions. The addition of 2 mg of naloxone injection in 500 mL of either solution provides a concentration of 0.004 mg/mL. Mixtures should be used within 24 hours. After 24 hours, the remaining unused mixture must be discarded. The rate of administration should be titrated in accordance with the patient's response. (See, e.g., The Syringe Driver: Continuous Subcutaneous Infusions in Palliative Care By Andrew Dickman, Jennifer Schneider and also Narcan Package Insert).

In the broadest sense, for purposes of the present invention, pharmaceutically active agent(s) which are not stable at high pH means that the pharmaceutically active agent(s) should or must be discarded after 24 hours when maintained at a pH greater than 7. In certain embodiments, "not stable at high pH" means that the pharmaceutically active agent may be chemically or physically unstable—it may degrade by about 10-25% over a time period of 180 days after constitution at a pH greater than 7; or it may fall out of solution (drug may precipitate) when dissolved; or it may settle over a short period of time when present in a dispersed state within a liquid thus making it unsuitable as a commercially viable product (e.g., that can be stored at room temperature).

For purposes of the invention, the term "stable in a low pH environment" means that the pharmaceutically active agent (e.g., opioid antagonist) in liquid 1 (pH≤5, or, e.g., pH from about 1 to ≤5) may be expected to be stable with less than 10% degradation of naloxone over 12 months.

In the broadest sense, for purposes of the present invention, pharmaceutically active agent(s) which are not stable at low pH means that the pharmaceutically active agent(s) should or must be discarded after 24 hours when maintained at a pH less than 7. In certain embodiments, "not stable at low pH" means that the pharmaceutically active agent may be chemically or physically unstable—it may degrade by about 10-25% over a time period of 180 days after constitution at a pH less than 7; or it may fall out of solution (drug may precipitate) when set aside, thus making it unsuitable as a commercially viable product (e.g., that can be stored at room temperature).

For purposes of the invention, the term "stable in a high pH environment" means that the pharmaceutically active agent in the composition 1 (pH≥7, or, e.g., pH from about 7 to 14) may be expected to be stable with less than 10% degradation of the pharmaceutically active agent over 18-24 months.

Opioid Antagonists:

The term "Opioid Antagonist" or simply "Antagonist" as used in connection with the present invention is meant to include full and partial antagonists and may include one or more of the following and/or derivatives: Naloxone, Naltrexone, methyl-naltrexone, 6β-naltrexol, Nalmefene, Nalorphine, Levallorphan, Cyprodine, Naltrindole, Axelopran, Bevenopran, Alvimopan, Nalbuphine, Naldemedine, Nalodeine and Norbinaltorphimine. It also includes mixed opioid agonist/antagonist drugs including without limitation nalbuphine, buprenorphine, pentazocine and butorphanol.

Pharmaceutical Actives:

The term pharmaceutical active or pharmaceutically active agent as used in connection with the present invention is meant to also include, in addition to opioid antagonists, any other pharmaceutical active or pharmaceutically active agent, including for systemic or topical delivery, and which may benefit from preparation and administration as set forth herein. Preferred pharmaceutically active agents are those suitable for rescue therapy (rescue drugs). For example, the pharmaceutical active agent may be a seizure rescue medication such as anticonvulsant benzodiazepines including, inter alia, alprazolam, midazolam, phenazepam, nitrazepam, lorazepam, flutoprazepam, etizolam, flubromazepam, diclazepam, diazepam, cloxazolam, clonazolam, clobazam and bretazenil. Another example may be the benzodiazepenes for anti-anxiety indication. For example, the pharmaceutical active agent may be a migraine rescue medication including inter alia sodium valproate, propranolol, metoprolol, topiramate, pregabalin, gabapentin and the triptans (sumatriptan, zolmitriptan, rizatriptan, naratriptan, frovatriptan, almotriptan and eletriptan) and any NSAID including, inter alia, acetylsalicylic acid, Diflunisal, Salicylic acid and other salicylates, Salsalate, Ibuprofen, Dexibuprofen, Naproxen, Fenoprofen, Ketoprofen, Dexketoprofen, Flurbiprofen, Oxaprozin, Loxoprofen, Indomethacin, Tolmetin, Sulindac, Etodolac, Diclofenac, Aceclofenac, Nabumetone, Piroxicam, Meloxicam, Tenoxicam, Droxicam, Lornoxicam, Phenylbutazone, Mefenamic acid, Meclofenamic acid, Flufenamic acid, Tolfenamic acid, Celecoxib, Nimesulide, Clonixin, Licofelone and Ibudilast.

For example, the pharmaceutical active may be a NSAID for pain rescue (e.g. post-operative pain, dental pain or other short term pain treatments) such as ketorolac, or any of the other NSAIDs listed above. The active may also be a narcotic analgesic for pain rescue such as morphine, oxycodone, buprenorphine, butorphanol, codeine, hydrocodone, hydromorphone, meperidine, methadone, nalbuphine, oxymorphone, pentazocine, propoxyphene, tramadol, tapentadol, oliceridine and fentanyl. These examples are non-limitative. As another example the pharmaceutical active may be ondansetron, scopolamine or other anti-emetics for post-operative or opioid-induced nausea.

The pharmaceutical active may include anti-emetics such as prochlorperazine, promethazine, ondansetron, granisetron, metoclopramide, droperidol, trimethobenzamide, and scopolamine.

It is expressly contemplated that combination therapies may be employed for treatment of multiple symptoms or for alleviating the side effect of one of the pharmaceutical actives. For example, a combination of an anxiolytic and an analgesic may be used for post-operative pain (e.g. diazepam with ketorolac). As another example a combination of an anti-emetic with an analgesic may be used for the emergency treatment of pain (e.g. scopolamine with nalbuphine). It is expressly contemplated that the present invention may be employed with new chemical entities as pharmaceutically active agents.

It is desired that, when the mixed mucosally absorbable composition is buccally administered to a human subject, the pharmaceutical active achieves a Tmax in plasma at less than ninety minutes (preferably at less than forty five minutes) with a therapeutic level in plasma reached within 30 minutes or fewer. It is desired that, when the mixed mucosally absorbable composition is intranasally administered to a human subject, the pharmaceutical active achieves a Tmax in plasma at less than twenty minutes, preferably less than fifteen minutes, more preferably less than ten minutes.

Excipients Useful for Mucosally Absorbable Formulations: Surfactants and Permeation Enhancing Agents:

Permeation enhancers that are useful to increase the absorption of the pharmaceutically active agent consist of the following with the more preferable permeation enhancers being the nonionic surfactants; however, at least most of the listed compounds below have utility as permeation enhancers. Effective amounts may be employed.

Anionic Surfactants:

Sodium octyl sulfate, Sodium decyl sulfate, Sodium dodecyl sulfate, Sodium tetradecyl sulfate, Sodium heptadecyl sulfate, Sodium eicosyl sulfate, Sodium laureth sulfate, Nicotine sulfate, Sodium taurocholic sulfate, Dimethyl sulfoxide, and Sodium tridecyl phosphate.

Zwitterionic Surfactants:

ChemBetaine CAS, ChemBetaine Oleyl, ChemBetaine C, Hexadecyldimethyl ammonio propane sulfonate, Decyldimethyl ammonio propane sulfonate, Dodecyldimethyl ammonio propane sulfonate, and Myristyldimethyl ammonio propane sulfonate.

Cationic Surfactants:

Benzyl pyridinium chloride, Dodecyl pyridinium chloride, Cetyl pyridinium chloride, Benzyldimethyl dodecyl ammonium chloride, Benzyldimethyl myristyl ammonium chloride, Benzyldimethyl stearyl ammonium chloride, Octyltrimethyl ammonium bromide, Decyltrimethyl ammonium bromide, Dodecyltrimethyl ammonium bromide, Myristyltrimethyl ammonium chloride, and Cetyltrimethyl ammonium bromide.

Nonionic Surfactants:

Sorbitan monolaurate, Sorbitan monopalmitate, Sorbitan monostearate, Sorbitan monooleate, Polyoxyethylene sorbitan monolaurate, Polyoxyethylene sorbitan monopalmitate, Polyoxyethylene (20) Cetyl Ether (Brij 58), Brij 97, Brij 30, Brij 56, and Triton X-, 100, Polyoxyethylene ethers, Polyoxyethylene esters, Polyethylene glycol esters, Sucrose esters, Sucrose ethers, D-alpha Tocopheryl polyethylene glycol 1000 succinate (TPGS or Vitamin E TPGS), Polyethoxylated castor oil (e.g Cremophor RH40), Poloxamers (eg. Pluronic F-127 or Kolliphor P407)

Fatty Acids:

Hexanoic acid, Octanoic acid, Decanoic acid, Undecanoic acid, Undecanoic acid, Dodecanoic acid, Tridecanoic acid, Myristic acid, Palmitic acid, Stearic acid, Oleic acid, Elaidic acid, Linoleic acid, Linolenic acid, and Cholic acid.

Fatty Esters, Glycerides and Oils:

Methyl hexanoate, Ethyl undecanoate, Methyl laurate, Methyl tridecanoate, Methyl myristate, Isopropyl myristate, Isopropyl palmitate, Palmityl palmitate, Diethyl sebaccate, Tetracaine, Glyceryl monolaurate, Glyceryl monooleate, and Ethylpiperazine carboxylate. Corn oil mono,di,tri-glycerides, D-alpha-Tocopherol, Fractionated triglyceride of coconut oil (medium-chain triglyceride), Fractionated triglyceride of palm seed oil (medium-chain triglyceride), Mixture of mono- and di-glycerides of caprylic/capric acid, Medium chain mono- and di-glycerides, Corn oil, Olive oil, Oleic acid, Sesame oil, Hydrogenated soyabean oil, Hydrogenated vegetable oils, Soybean oil, Peanut oil, Beeswax.

Sodium Salts of Fatty Acids:

N-Lauryl sarcosinate, Sodium caprylate, Sodium decanoate, Sodium palmitate, and Sodium oleate.

Fatty Amines:

Octyl amine, Decyl amine, Dodecyl amine, Tetradecyl amine, Oleyl amine, and Urea.

Azone-Like Molecules:

Methyl pyrrolidone, Cyclohexyl pyrrolidone, Octyl pyrrolidone, Decyl pyrrolidone, Decyl methyl pyrrolidone, Methyl piperazine, Phenyl piperazine, Octanamide, Hexadecanamide, and Caprolactam.

Others:

Carveol, Pinene oxide, Limonene, Menthol, Pulegone, Carvacrol, Pinene, Menthone, Terpineol, Cineole, Fenchone, Trimethoxy propylene methyl benzene, Linalool, Geraniol, Octyl dodecanol, Phospholipids, Cyclodextrins, Chitosans, Dimethyl sulfoxide (DMSO).

Chelators:

The term "Chelator" as used in connection with the present invention is meant to include at least one or more of the following: Ethylene Glycol Tetraacetic Acid and salts thereof (EGTA), Ethylene Diamine Tetraacetic Acid and salts thereof (EDTA), Itoic Acid, Kojic Acid, Catechol Amines, Siderophores, Hydroxamate, siderophores (ferrichrome, mycobactin, desferrioxamine, pseudobactin, aerobactin, rhodoto rulic acid, mugineic acid), histidine, cysteine, purines, pyrimidines, metalloenzymes, transport proteins, citrate, malate, histamine, adrenaline, cytochromes, spemidine. EDTA is especially useful. Effective amounts may be employed.

Antioxidants:

Antioxidants useful in connection with the present invention include primary and secondary antioxidants, including thiols, polyphenols such as Vitamin C, Tocopherols, Carotenes, Ubiquinol, Glutathione, Lipoic Acid, Eugenol, Lycopene, Resveratrol, Flavonoids, Lutein, butylated hydroxy anisole (BHA), tertiary butyl hydroquinone, and butylated hydroxy toluene (BHT) are useful. BHA, BHT are especially useful as is Vitamin C and Tocopherols. Effective amounts may be employed.

Crystallization/Precipitation Inhibiting Excipients:

Crystallization inhibitors useful in connection with the present invention include polyvinyl pyrrolidone (PVP), polyethylene-polypropylene glycol copolymers (Pluronics™), inulin lauryl carbamate, polyacrylate, hydroxypropyl methylcellulose (HPMC), HPMC with low glass transition temperature (Affinisol), hydroxypropyl methylcellulose acetate succinate (HPMCAS), Vinyl Pyrrolidone-Vinyl Acetate Co-Polymer (e.g Kollidon VA64), Caprolactam/polyvinyl acetate/polyethylene glycol copolymer (Soluplus). Effective amounts may be employed.

Polyols:

The term "polyol" as used in connection with the present invention is meant to include one or more of the following: sugar alcohols, including maltitol, sorbitol, xylitol, lactitol, erythritol, hydrogenated starch hydroxysates, isomalt, glycerin, pentaerythritol, ethylene glycol, and mannitol. Effective amounts may be employed.

Buffers:

Buffer compositions useful with the present invention are set forth below:

Pharmaceutically acceptable buffers of pH 5 or greater that are useful for the immediate adjustment of the active (e.g. naloxone) at the point of use and include one or more of the following (without limitation): Citric Acid/Potassium Dihydrogen Phosphate, Monosodium Phosphate/Disodium Phosphate using phosphoric acid to lower the pH or sodium hydroxide to raise the pH, Citric acid/Sodium citrate, DL-Cysteine/Sodium DL Cysteinate, Boric Acid/Sodium Hydroxide, Sodium Bicarbonate/Sodium Carbonate. Also, biologically acceptable strong bases may be used in the buffer compartment, which may include Calcium hydroxide, Magnesium hydroxide, Aluminum hydroxide, Magnesium acetate, sodium hydroxide, calcium carbonate, potassium hydroxide, sodium carbonate, potassium carbonate etc. These same buffers can be used for stability protection where the active ingredient is stable at a basic pH, and may be a direct combination with the active ingredient. These buffers may also be used to effect a basic pH at the point of use. Effective amounts may be employed.

Other acids or acidic buffers are useful for the stability protection of the antagonist and are in direct combination with the active ingredient (or, for adjustment at the point of use where the active ingredient is best absorbed at an acidic pH). These acids or buffers will include all systems that will create a pH less than 5, most preferably 3 or less and can include one or more of the following (without limitation): Formic Acid/Sodium Formate, Hydrogen Chloride/Potassium Chloride, Hydrogen Chloride/Glycine, Hydrogen Chloride/Potassium Hydrogen Phthalate, Citric Acid/Sodium Citrate, Acetic Acid/Sodium Acetate, Citric Acid/Disodium Hydrogen Phosphate, Citric Acid/Trisodium Citrate Dihydrate, etc. Effective amounts may be employed.

In certain embodiments of the present invention, buffers leverage the pH-solubility profile of the drug to induce super saturation after combination of the liquid containing compartments.

Polymer Viscosifiers, Gel Formers and Mucoadhesive Agents:

The term "Water Soluble Polymer" as used in connection with the present invention and is intended to include one or more of the following polymers for imparting viscosity to the liquid and/or forming a gel: pullulan, hydroxypropyl methylcellulose (HPMC), hydroxyethyl cellulose (HEC), hydroxypropyl cellulose (HPC), polyvinyl pyrrolidone (PVP), carboxymethyl cellulose, polyvinyl alcohol, sodium aginate, polyethylene glycol, xanthan gum, chitosan, tragancanth gum, guar gum, acacia gum, arabic gum, polyacrylic acid, methylmethacrylate copolymer, carboxyvinyl copolymers, Crosslinked polyacrylic acid polymer (Carbopols), polycarbophils (acrylic acid polymer cross-linked with divinylglycol), starch, gelatin, Carbomers, Poylyethylene Oxides, carrageenan, pectins and combinations thereof.

As used herein the phrase "water soluble polymer" and variants thereof refer to a polymer that is at least partially soluble in water, and desirably fully or predominantly soluble in water, or absorbs water or may form colloidal dispersions in water. The materials useful with the present invention may be water soluble at room temperature and other temperatures, such as temperatures exceeding room temperature. Moreover, the materials may be water soluble at pressures less than atmospheric pressure. Desirably, the water soluble polymers are water soluble having at least 20 percent by weight water uptake. Dosage forms of the present invention formed from such water soluble polymers are desirably sufficiently water soluble to be dissolvable upon contact with bodily fluids. Effective amounts may be employed, including sufficient amounts to form a gel and maintain a gel against expected salivary flow (or other bodily fluid) for longer than five minutes, preferably for longer than ten minutes.

The system does not have to start as a gel and envisioned are gels that are formed in-situ when the two fluids from the chambers are brought together during use. There are certain polymers, which on their own can increase viscosity when used at low levels but when mixed with certain other excipients the viscosity changes to a semi-solid gel. Non-limitative examples of such systems are carrageenan+a mono, di, trivalent cation such as calcium; gellan gum+a mono, di, or trivalent cation; sodium alginate+a cation. There are other viscous polymers that are synergistic with other polymers and will form gels such as xanthan or kappa carrageenan with locust bean gum. Also envisioned are shear thinning gels which upon mechanical shear will become quite fluid to enable complete evacuation of the fluids from each compartment but will set to a gel very quickly once the shear is removed. An example of such a system is gellan gum. Also envisioned are thermo-reversible gels, which are low viscosity at room temperature but upon entering the oral cavity (or other bodily cavity like vaginal or rectal) at body temperature will quickly form a gel. One such system uses block copolymers and a non-limitative example of such a system is Pluronic F127 alone or mixed with other polymers.

Polar Solvents and Co-Solvents

Ethanol, Propylene glycol, Polyethylene glycol, Propylene carbonate, DMSO, Tetrahydrofurfuryl alcohol polyethylene glycol ether (Glycofurol), propylene glycol monolaurate, propylene glycol monocaprylate and diethylene glycol monoethyl ether.

Other Useful Excipients:

The present invention includes the use of certain excipients for identifying a change in pH, such as phenol red, bromothymol blue, bromo cresol purple, bromo phenol blue, litmus granules, neutral red, thymol blue, methyl orange and phenolphthalein. Also included is the use of FD & C colors and their color change to determine when fluid from chamber one mixes with fluid from chamber two. An example of such a system is yellow #5 in one chamber and blue #1 in the other chamber when brought together form green. Flavors, sweeteners and fillers are also envisioned as well as surface active agents. Effective amounts may be employed.

Super Saturation and Transient Stability:

The present invention contemplates the use of precipitation inhibitors to maintain super saturation of acidic or basic pharmaceutical active(s) in combined liquid, and the use of a transiently stable combined liquid for mucosal delivery of pharmaceutical actives. The supersaturation is a means to provide higher thermodynamic activity that enhances absorption compared to a simple solution of the drug. For rapid mucosal delivery of permeable drugs, the maintenance of a state of supersaturation (where the concentration of solute within the solution is above the thermodynamic equilibrium solubility) needs only to be very transient (<20 minutes). The state of supersaturation is invoked by a rapid change in the solubility effected by the rapid pH change or rapid dilution. The transient supersaturation may lead to very rapid mucosal drug absorption if the speed of drug precipitation and reversion to equilibrium from this metastable state of high thermodynamic activity is slowed down for long enough by the use of suitable polymeric precipitation inhibitors.

For example, the naloxone HCl salt is soluble in water and is reported to be >50 mg/g and also as high as 200 mg/g. The reported solubility of the base form of Naloxone is 1,400 mg in one liter of water or 1.4 mg/g of water. See, US EPA. [2012]. Estimation Programs Interface Suite™ for Microsoft® Windows, v 4.11 or insert version used]. United States Environmental Protection Agency, Washington, D.C., USA. (Naloxone HCL solubility in water: 73 mg/mL; Naloxone free base solubility in water, 1.4 mg/mL at 25 deg C. (estimated)), the content of which is incorporated herein by reference. Naloxone evidently possesses the suitable physicochemical properties and sufficient permeability to function as an effective CNS drugs—it has sufficient aqueous solubility while also possessing the lipophilicity to cross the blood-brain barrier and indeed also sufficient to cross the nasal mucosa at sufficiently rapid rates (a nasal spray formulation is approved for use). However, an oromucosal formulation does not yet exist because the buccal mucosal barrier represents a comparatively more formidable barrier due to the greater thickness of the keratinized membrane and smaller surface area. In the present invention, when the naloxone low pH gel is combined with the high pH buffer gel, there is a rapid change in the pH of the entire system as it becomes alkaline and the drug exceeds its equilibrium solubility at those conditions. The concentration of 30 mg of naloxone base per gram of water is more than 20 times the amount of free base form expected to be soluble. Therefore, a super-saturated state exists—temporarily—until phase change occurs in the form of crystallization. In the present invention, certain excipients are used to slow down the crystallization process—thereby effecting a transient stability. The slowing down or inhibition of crystallization is required—in the case of naloxone the charged ionic species in solution loses its charge at higher pH and would instantly crystallize due to its inherent insolubility. Thus, it is an object of the present invention to make a transiently stable formulation of a super saturated solution. In the primary embodiment, the transiently stable supersaturated solution in a liquid formulation for use in rescue therapeutic applications by an oromucosal route and with the supersaturated solution being compounded just prior to administration. Similarly, embodiments of the present invention may be directed to other mucosal sites and any pharmaceutical active.

In the preferred embodiment, the compounded product is a gel because over-dilution of the gel formulation with saliva (and or other bodily fluids at the administration site) would not only reduce the concentration of drug (which reduces the driving force for absorption) but also reduces the effectiveness of the crystallization inhibitors because their overall concentration is lowered. Thus, such salivary (or bodily fluid) dilution will tend to reduce the time period during which the dosage form is transiently stable, whereas it is Applicant's intention to increase or maximize the time period during which the dosage form is transiently stable.

In the preferred embodiment, it is desirable to formulate the two starting solutions—typically gels—at the right viscosity such that the two starting solutions (typically gels) mix intimately during compounding and spread sufficiently in the oral cavity but remains as a distinct semi-solid phase that resists dilution of the drug and polymers—hence the need for a formulation with balanced viscosity characteristics. It is also important to note that that the pressure required to mix the starting solutions must be proportionate to the hand strength of a typical user in a situation that requires manual dexterity to aim the dosage form into the intended oromucosal cavity or other mucosal surface. If the pressure exceeds or challenges the hand strength of the user, dexterity and dosage form placement will be less accurate.

Upon crystallization of the active drug, its absorption across the mucosa may be expected to slow down significantly. Since the "absorption time window" for the naloxone (and many other) rescue therapeutic is about 15 minutes, preferably ten minutes, more preferably under five minutes, the crystallized form is not desirable and needs to be delayed for that period of time. By "absorption time window" Applicant means the time period during which the active ingredient reaches blood levels that are considered to exert therapeutic effect based upon known pharmacokinetic-pharmacodynamic relationships. This will depend upon the nature of the rescue situation, and the time period for other existing therapies (typically using other routes of administration) to reach efficacious blood levels.

Because the oromocusal route of administration is more convenient, safer (no needle stick risk), and requires less training than injection, is likely faster than existing oral therapies, and may otherwise be more convenient compared to existing therapies (e.g. rectal administration of diazepam), marginal increases in the time to reach efficacious blood levels comparable with injectable and intranasal routes may be an acceptable trade-off for the benefits of oromucosal delivery.

The use of two liquid gels, a delivery/mixing device, and at least one crystallization inhibitor excipient, allows the finished buffered formulation to reach a super-saturated state at the point of use thereby delivering a high concentration of solubilized un-ionized or protonated form of the active of a given pKa directly to the mucosal tissue. Although the pH is not conducive to physical or chemical stability, the absorption of the drug occurs too rapidly for crystallization and/or degradation to substantially occur.

As the canine and human models discussed in the examples 3, 4 and 10 below indicate, the Applicant was able to obtain surprising results—essentially equaling absorption of buccally delivered drug as compared with the approved intranasal spray, Narcan®.

The canine example below is important because it demonstrates effective, rapid uptake of drug using the present invention where the subject animal is in opioid induced respiratory distress. This is important in the case of naloxone, which is typically administered to patients in distress, and yet clinical studies to approve the medication are typically performed upon healthy patients.

In the primary embodiment, a single bolus is used, however it is also possible to delivery multiple boluses particularly where a higher dose is required.

The same approach for creating a supersaturated state by rapid change in the pH of a solution may be carried out in the reverse direction for an acidic drug, for example ketorolac for the treatment of pain. The acidic drug is present as a solution in water (or water plus alcohol or other water-miscible polar co-solvents) and may also have polymer/s to provide a viscous liquid or semi-solid or gel-like consistency. It may be at neutral pH or have a basic component or a buffer pair to bring the pH to the basic region above pH 7 to improve drug stability and maintain equilibrium solubility. This gel is combined prior to use with an acidic buffer gel. When the ketorolac gel at high pH is combined with the low pH buffer gel, there is a rapid change in the pH of the entire system as it becomes acidic and the drug exceeds its equilibrium solubility at those conditions. Therefore, a super-saturated state exists—temporarily—until phase change occurs by crystallization of the drug. The transiently stable supersaturated solution of ketorolac with the super-saturated gel solution being compounded just prior to administration is suitable for oromucosal or other mucosal use in the rapid treatment of pain indications. Phase change may be delayed through use of crystallization inhibitors.

It must be noted that unlike basic drugs, in the case of acidic drugs, the supersaturated state of the drug may continue to exist even after the gel is swallowed after initial buccal application. This is because the gastric pH, especially in the fasted state may be similarly low as the combined gel. This may allow the continued maintenance of the unionized protonated species in solution for a longer period of time, however, the rate of absorption may fall due to dilution within a large volume of gastric fluid.

The state of supersaturation may also be invoked by a rapid change in the solubility effected by rapid dilution with a solvent in which the drug is insoluble.

For example, the therapeutic dose of diazepam (5-15 mg) is relatively poorly soluble in water (0.012 mg/ml) and across the physiological pH range. However, diazepam is quite soluble in lipidic excipients and this fact may be leveraged to produce a drug-containing gel formulation that serves as a lipidic pre-emulsion component of an oil-in-water combined gel. The pre-emulsion phase may contain lipid solvents, amphiphilic co-solvents, surfactant and surfactant combinations as well as precipitation/crystallization inhibitors. Upon combination of the pre-emulsion and the acidic buffer a visually isotropic microemulsion is formed. This maintains the drug as an apparent solution achieving a solubility of 10 mg/g without any microscopic evidence of crystal growth. The dispersed internal phase of the microemulsion contains drug at high apparent solubility. The fraction of dissolved diazepam in the acid-buffered continuous phase remains predominantly unionized and may exist as a supersaturated solution at the pH of maximum absorption. The dispersed oily phase may also be saturated with aqueous phase and may now have reduced solubility for the drug which may exist as a supersaturated solution within micellar or multi-lamellar liquid crystal structures or as a microemulsion or nanoemulsion.

See, Gao P, Rush B D, Pfund W P, Huang T, Bauer J M, Morozowich W, Kuo M S, Hageman M J. (2003). Development of a supersaturable SEDDS (S-SEDDS) formulation of paclitaxel with improved oral bioavailability. J Pharm Sci, 92, 2386-2398; Gao P, Morozowich W. (2006). Development of supersaturatable self-emulsifying drug delivery system formulations for improving the oral absorption of poorly soluble drugs. Expert Opin Drug Deliv, 3, 97-110; and Using polymeric precipitation inhibitors to improve the absorption of poorly water-soluble drugs: A mechanistic basis for utility. Dallas B. Warren, Hassan Benameur, Christopher J. H. Porter, and Colin W. Pouton, Journal of Drug Targeting, 2010; 18(10): 704-731, the contents of which are incorporated herein by reference.

Some site-specific concerns may apply where the point of use is the mucosal tissue of the nasal cavity (i.e. intranasal delivery). Mucosal tissue of the nasal cavity is generally understood to be a membrane more readily traversed by pharmaceutical actives, due inter alia to the rich vascular plexus of the nasal cavity. Despite the relative ease of traversing nasal membranes (as compared with other mucosal sites, e.g. the buccal mucosa), embodiments of the present invention can be useful to with intranasal delivery of pharmaceutical actives, particularly where such actives are not readily, rapidly or otherwise insufficiently absorbed through standard formulation strategies.

Applicant has demonstrated that embodiments of the present invention can offer substantial, surprising improvements in PK performance as compared with existing drug products (the comparator). The comparator may be an existing, approved drug or a formulation that is not approved but for which PK data otherwise exists. For example, the comparator may be a formulation reported in the literature.

The comparator may be the same (or different) route of administration. In the Examples below, Applicant describes an embodiment of the present invention that buccally delivers diazepam with improved PK performances relative to the approved, rectal diazepam (Diastat). Applicant describes an embodiment of the present invention that intranasally delivers naloxone with improved PK performance relative to the existing approved naloxone nasal spray. Applicant describes an embodiment of the present invention that intranasally and intraorally (sublingually or buccally) delivers nalbuphine with improved PK performance relative to oral and parenteral versions of nalbuphine described in the literature. Applicant describes an embodiment of the present invention that buccally delivers ketorolac with improved PK performance relative to approved oral and intranasal versions of ketorolac.

Applicant does not only describe embodiments of the present invention with improvements in PK performance relative to a comparator. Applicant also describes embodiments where PK performance is nearly as good as a comparator where the comparator uses a less challenging route of administration. For example, Applicant describes an embodiment of the present invention that delivers naloxone buccally with PK performance that is nearly as good as the approved nasal spray.

It is preferable that comparisons in PK performances be made at the same dose. However, comparisons may also be made on a dose adjusted basis, preferably where there is linearity/proportionality of PK response up to the dose administered.

For example, nalbuphine hydrochloride is understood to have a bioavailability when delivered orally of approximately 12%. Surprisingly, Applicant achieved more than double the bioavailability (200%) for intranasally delivered nalbuphine hydrochloride on a dose adjusted basis using an embodiment of the present invention, as further described in example 14.

In certain embodiments of the present invention, an intranasally delivered pharmaceutical active will have 35% or more greater relative bioavailability than when the drug is delivered in conventional oral form (i.e. tablet or capsule) or intraoral form, preferably 50% or more greater, more preferably 80% or more greater bioavailability, most preferably 125% or more greater bioavailability and even more preferably more than 250% greater bioavailability than when delivered in conventional oral form or intraoral form. Such results may similarly be achieved using embodiments of the present invention for other mucosal sites (i.e. buccal, sublingual, rectal vaginal), as compared with oral form or intraoral form. These bioavailability improvements may similarly be achieved relative to other comparator routes of administration (i.e. intranasal, buccal, sublingual, vaginal, rectal).

In certain embodiments of the present invention, an intranasally delivered pharmaceutical active may achieve peak plasma concentration (Tmax) faster than when an equivalent dose of the drug is delivered orally in conventional form (i.e tablet or capsule) or intraorally, 25% to 1500% faster, preferably more than 100% faster, more preferably more than 200% faster, even more preferably more than 500% faster, still more preferably more than 800% faster. In the case of nalbuphine delivered intranasally using an embodiment of the present invention, peak plasma was achieved approximately ten times—1000%—faster than intraoral administration as reported in the literature (see Example 14 below). Such improved results may similarly be achieved using embodiments of the present invention for other mucosal sites (i.e. buccal, sublingual, vaginal, rectal), including with different route of administration comparators.

In certain embodiments of the present invention, an intranasally delivered pharmaceutical active may achieve a maximum drug plasma concentration that is greater after intranasal administration than when the drug is delivered in conventional oral form (i.e. tablet or capsule) or intraoral administration. Such maximum drug plasma concentration may be approximately or more than 50% higher, preferably approximately or more than 150% higher, approximately or more preferably more than 300% higher and most preferably or more than 500% higher. In the case of the Example 14 below, Applicant achieved a maximum nalbuphine drug plasma concentration, after intranasal delivery of an embodiment of the present invention, approximately five times (500%) higher than that achieved by an equivalent dose of the drug administered as a conventional oral formulation. Such results may similarly be achieved using embodiments of the present invention for other administration sites (i.e. buccal, sublingual, vaginal rectal) as compared with other comparator administration sites.

As demonstrated in the intranasal examples below, surprising results were achieved with very rapid Tmax using embodiments of the present invention delivered intranasally. Such Tmax may occur within thirty minutes, preferably within twenty minutes, more preferably within 12.5 minutes, yet more preferably within ten minutes, and most preferably within 7.5 minutes.

Embodiments of the present invention may also achieve surprisingly rapid Tmax using the buccal, sublingual, vaginal or rectal routes. For example, Tmax may be achieved within 60 minutes, preferably within 45 minutes, more preferably within 30 minutes.

Embodiments of the present invention may also achieve PK results that are nearly as good as another route of administration, where the compared route of administration is understood to be easier to penetrate with drug (e.g. buccal versus intranasal). For example, a buccal embodiment of the present invention may achieve Tmax, Cmax and AUC that is nearly as good as an intranasal version of the same drug. Tmax may be 30% slower or less, preferably 20% slower or less, more preferably 10% slower or less. Cmax may be 30% lower or less, preferably 20% lower or less, more preferably 10% slower or less. AUC may be at least 70% of the comparator, preferably at least 80% of the comparator, more preferably at least 90% of the comparator.

Special consideration should be given to the physical size of the dose (as distinct from the dose of active drug) where the present invention is employed intranasally. While the nasal cavity is itself large, the user may experience discomfort and nasal blockage if too much solution volume is delivered. Still, particularly where lower viscosity formulations are employed (1-3000 cp), the inventor has discovered that relatively large amounts of liquid can be comfortably delivered to the nasal cavity. For example, greater than or equal to 500 mg of liquid to less than or equal to 1.75 g, or greater than or equal to 750 mg to less than or equal to 1.25 g. Applicant notes that such volumes are significantly larger than used in approved intranasal products (the largest volume Applicant could identify was Natesto® which uses 244 mg of gel, administered in two 122 mg actuations).

Where the embodiments of the present invention are used intranasally, relatively lower viscosity and relatively higher flowability of the composition may be desirable to increase the coated area of the nasal mucosa, and or the flow and spreading of the product over a larger geography of the nasal cavity's mucosa.

An additional advantage of the nasal mucosa site, as compared with oromucosal sites, is the lower potential for dilution by secretions in the nasal mucosa. This means that the administered composition is less likely to be quickly diluted from salivary secretions. This allows the pH to remain in the intended range of maximum absorption because the buffer capacity of the formulation is not quickly exceeded. The duration of the existence of the uncharged species may therefore be longer in the case of nasal administration as compared with buccal or sublingual administration. Additionally, lower salivary wash out (e.g. swallowing) means the time period the pharmaceutical active is in mucosal contact prior to swallowing may be longer, as compared with buccal or sublingual use.

Nasal mucosa sites may be particularly suitable when delivering pharmaceutical actives with a low log p value, e.g. less than or equal to 1.5.

Nasal mucosa sites may be particularly suitable when delivering pharmaceutical actives for which oral formulations are understood to have low bioavailability in standard oral formulations (i.e. tablet, capsule), i.e. less than 25%, or less than 20%, or less than 15%.

The nasal mucosa—being more subject to irritation than the oral mucosa—is understood to tolerate pH ranges of approximately 3 to 10. It is desirable that embodiments of the present invention intended for nasal use have a pH in the range of 3 to 10, even where absorption may be favored by a more extreme pH outside of the 3 to 10 range.

In the case of intranasal delivery, the intended dose may be delivered to one, or both nostrils, either contemporaneously, or sequentially. In some cases, follow on intranasal doses will be given on an as needed basis.

Embodiments of the present invention may be used to allow for non-parenteral delivery of pharmaceutical actives not otherwise available in commercially approved non-parenteral form. In certain embodiments, intranasal formulations will comprise a flavor or other olfactory agents for pleasing aroma, or to mask flavors in the case of any product reaching the mouth.

In certain intranasal formulations, it may be desirable to include a sensory agent in effective amounts to substantially mitigate sensory response to particularly acidic or basic formulations. Embodiments of the present invention may be used buccally, sublingually, intranasally, vaginally, rectally and intraocularly.

In the case of vaginal delivery, embodiments of the present invention may be used to effect rapid, preferential delivery of a pharmaceutical agent to the uterus using the first uterine pass effect.

EXAMPLES

The following examples demonstrate certain embodiments of the invention. Many variations of these formulations are feasible and the examples are meant for illustrative purposes only and are not meant as all encompassing. Any combination of pH values may be used based upon the stability and absorption properties of the drug being formulated and the desired pH of the individual chambers and combined gel.

Example 1

A 1 kg batch of a solution with a carbomer gelling agent is prepared as follows. Percentages are w/w % of the final 1 kg batch.

Purified water (96.45%; 964.54 g) is added to a 0.5 gallon kettle equipped with a mixing apparatus (counter-rotating mixer or propeller mixer). The water is heated to about 40° C. and is stirred. The temperature is maintained, the stirring speed is increased to about 1200 RPM, and Carbomer 940 (0.546%; 5.46 g) is slowly added until a homogeneous mixture is formed. The mixture is stirred for an additional 45 minutes at about 40° C. and propylene glycol (3%; 30 g; heated to about 40° C.) is added to the mixture and stirred for 15 minutes. Water is added back to the mixture to obtain 1000 grams and mixing is continued at about 12 RPM, avoiding aeration. The temperature is maintained for about 15-30 minutes to form Liquid Mixture A. Separately, two buffers are prepared. The first buffer is prepared at a target pH of 5.8 and the second buffer is prepared at a target pH of 8. The first buffer of pH 5.8 contains 0.207 ml of 2 mol/l of Acetic Acid and 2.294 ml of a 2 mol/l of Sodium Acetate. The second buffer of pH 8 contains 0.204 ml of a 2 mol/l of sodium dihydrogen phosphate and 2.296 ml of a 2 mol/l of disodium hydrogen phosphate. The buffers are designated as Buffer 5.8 and Buffer 8.

Five hundred grams of Liquid Mixture A is weighed into a separate stirring vessel and the 5.8 buffer is added with slow mixing. The mixture is stirred under 28 in. Hg. vacuum for 12 minutes and is designated Liquid Mixture B.

Five hundred grams of Liquid Mixture A is weighed into a separate stirring vessel and buffer 8 is added with slow mixing. The mixture is stirred under 28 in. Hg. vacuum for 12 minutes and is designated Liquid Mixture C.

In a separate mixing procedure a repeat of Liquid Mixture A is performed into which 12.2 grams of Naloxone HCl is added. The pH is adjusted to 3 using citric acid and sodium citrate. EDTA (1% wt/wt %) is added to the solution. This will equate to 10 mg of Naloxone base per gram of gel and is designated Liquid Mixture D.

One gram of Liquid Mixture D is added to compartment 1 of FIG. 1-6 of the two sided pouch or syringe and one gram of Liquid Mixture B is added to the other compartment 2 of FIG. 1-6 of the pouch or syringe. The gels are combined prior to use and extruded, from the package (labeled part 6 in FIGS. 1-6) and the sample is designated Combined Gel Mixture 1 at 5.8 pH.

One gram of Liquid Mixture D is added to the first compartment 1 of FIG. 1-6 of the two side pouch or syringe and one gram of Liquid Mixture C is added to the other compartment 2 of FIG. 1-6 of the pouch or syringe. The gels are combined prior to use and extruded, from the package (labeled part 6 in FIGS. 1-6) and the sample is designated Combined Gel Mixture 2 at pH 8.

Example 2

HPMC E15+Polyethylene Oxide N80+Maltitol at a ratio of 2:1:1 are combined with 1% (wt. %) Citric Acid and 1% (wt. %) Edetate Disodium and 1% (wt. %) Etocas 35 and 0.5% (wt. %) Glycerol Monooleate. The combination (20 grams) is combined with water (80 grams) and stirred for 3 hour using a gate impeller. During the last hour of mixing, vacuum was set at 27-28 inches of Hg to deaerate the mixture. To 97.58 grams of this mixture is added 2.42 grams of naloxone HCl dihydrate to obtain 20 mg of Naloxone base per gram of polymer gel solution. This mixture is designated as Liquid Mixture A2.

Another polymer mixture of 20 grams is made using HPMC E15+PEO N80+Maltitol+Propylene Glycol Alginate in 2:1:1:1 ratio. The polymer blend is added to 75 grams of water. To this mixture 4 grams of a buffer pH 8 is added, which contains 0.204 ml of a 2 mol/l of sodium dihydrogen phosphate and 2.296 ml of a 2 mol/l of disodium hydrogen phosphate, and 1 gram of Glycerol Monooleate are added to the polymer mixture and the combination is mixed 3 hours using a gate impeller. During the last hour, vacuum is applied at 27 to 28 in Hg. to deaerate the polymer mixture. This mixture is designated as Liquid Mixture B2.

One gram of Liquid Mixture A2 (20 mg of Naloxone base) is added to compartment 1 of FIG. 1-6, and one gram of Liquid Mixture B2 is added to the other compartment 2 of FIG. 1-6. The gels are combined prior to use and extruded, from the package (labeled part 6 in FIGS. 1-6) and the sample is designated Combined Gel Mixture 3 at pH 8.

Example 3

A prototype antagonist formulation was prepared consisting of two component gels, Liquid Mixture A and Liquid Mixture B. This formulation was tested in a preliminary animal study. Table 1 shows the composition of Liquid Mixture A. Liquid Mixture A was made in the following manner.

Ingredients 1, 2, 3, 4, 5 and 7 were dry blended together. Ingredient 6 and 8 were added to a 250 ml beaker and mixed for 20 minutes using a magnetic stirrer. Ingredients 1, 2, 3, 4, 5 and 7 were added slowly to the beaker with continued stirring. Once all the ingredients were wetted the mixture was sealed and placed in a refrigerator (2-8° C.) for 24 hrs. After 24 hours the solution/suspension was removed and allowed to reach room temperature. A drop placed on the skin gelled upon contact indicating a proper thermal gelation at body temperature. The sample was designated as Liquid Mixture A pH 3.0. A quantity of naloxone slightly in excess of the solubility limit of naloxone at room temperature was added to the Liquid Mixture A pH 3.0.

TABLE 1

| (Example 3). pH 3.2 Naloxone Liquid Mixture A | | |
|---|---|---|
| Ingredient Number | Name | Amount (grams) |
| 1 | Pluronic F127 | 16.22 |
| 2 | Sorbitol | 2.0 |
| 3 | Citric Acid | 0.37 |
| 4 | Na Citrate | 0.16 |
| 5 | EDTA | 0.04 |
| 6 | Brij 58 | 1.0 |
| 7 | Naloxone HCl 2H$_2$O | 6.34 |
| 8 | Water | 73.87 |
| TOTAL | — | 100.0 |

Liquid Mixture B composition is shown in table 2 below. Liquid Mixture B was made in the following manner.

Ingredient 4 was added to a 250 ml beaker and stirred with a magnetic stirrer. Ingredients 1, 2 and 3 were dry blended and added slowly to the beaker and stirred with the magnetic stirrer until all ingredients were wetted. The mixture was placed in a refrigerator (2-8° C.) for 24 hrs. After 24 hours the solution was brought to room temperature and a drop placed on the skin gelled upon contact indicating a proper thermal gelation at body temperature. The sample was designated Liquid Mixture pH 10. This was Liquid Mixture B.

TABLE 2

| (Example 3). pH 10 Liquid Mixture B | | |
|---|---|---|
| Ingredient | Ingredient | Weight |
| 1 | NaOH | 0.6 |
| 2 | NaHCO3 | 3.0 |
| 3 | Pluronic | 17.3 |
| 4 | Water | 79.05 |
| TOTAL | — | 100 |

It was found in the laboratory that when this combined gel was added to 1 g of human saliva at pH 6.23, a final pH of 8.26 was achieved. This demonstrated that the pH at site of absorption is high enough to insure proper absorption of the Naloxone. 1 g of low pH gel contains 63.4 mg of Naloxone HCl dihydrate and will require 2.6 grams of the Combined Gel Mixture in the 1:1.6 ratio of Liquid Mixture A and Liquid Mixture B.

First Animal Opioid Reversibility Study.

This formulation was used in a preliminary animal overdose reversibility study which was presented in the parent application. Two Beagle dogs approximately 10 months old, weighing 11.3 kg and 10.5 kg were used in this study. The animals were fasted overnight, weighed, and observed for clinical observations, including baseline heart and respiration rates. Fentanyl citrate (concentration—0.05 mg/mL) via slow bolus intravenous injection was used to achieve sedation. Once sedation was reached, the components of the test article (Liquid Mixture-A and Liquid Mixture B) were combined using a dual syringe system to form a Combined Gel Mixture. The Combined Gel Mixture (Liquid Mixture A+Liquid Mixture B) when given at a total dose of 5.5 mg/kg resulted in a recovery from sedation which required seven minutes whereas increasing the dose to 8.9 mg/kg resulted in a recovery from sedation requiring only five minutes. A second dose ranging animal study using lower doses and a slightly modified formulation was subsequently conducted as shown in Example 4.

Example 4

Second Animal Opioid Overdose Reversibility Study

A second animal overdose reversal study was conducted at three different doses using the formulations shown in Table 3-6 below which were prepared in a manner similar to that described in Example 3. Opioid non-naïve male, healthy, fasted beagle dogs between 2.5 and 5.5 years of age, and ranging from 8.5 to 13.0 kilograms in weight at study initiation, were utilized for this study. An opioid agonist, fentanyl citrate, was administered intravenously (IV) as a slow bolus into the cephalic vein via an indwelling catheter followed by a 1 mL flush with normal saline. Fentanyl was initiated at 0.005 mg/kg and was increased up to 0.250 mg/kg to achieve sedation characterized by recumbence/reluctance to stand, central nervous system (CNS) depression (head hung low), ataxia, decreased response to stimuli, slow response to toe pinch, bradycardia (<70 bpm), miosis, and/or decreased respiratory rate (<16 breaths per minute). Once opioid sedation symptoms had been achieved, test article was administered into the buccal cavity of the animal.

Three different doses (4 mg, 8 mg & 30 mg) were administered to the animals. The 4 mg and 8 mg were provided by administering 1 mL (0.5 mL Gel A+0.5 mL Gel B) or 2 mL (1 mL Gel A+1 mL Gel B) respectively of the gel compositions in Table 3 and 4 below. A more concentrated formulation was used to administer 30 mg of naloxone by combining 1 mL of Gel A and 1 mL of Gel B as shown in Table 5 and 6 below. In this manner, the effective concentrations of the drug in the three combined gel doses were 2 mg/g, 4 mg/g and 15 mg/g respectively for a corresponding total administered dose of 4 mg, 8 mg & 30 mg. The dosing was carried out using a double barrel syringe fitted with a mixing nozzle similar to that shown in the FIG. 5. Two control animals were also included in the study.

TABLE 3

(Example 4). Naloxone 8 mg/g Gel-A, pH 3.5

| Ingredient Number | Name | Amount |
|---|---|---|
| 1 | Pluronic F127 | 14.47 |
| 2 | Sorbitol | 2.04 |
| 3 | Citric Acid | 0.38 |
| 4 | Na | 0.16 |
| 5 | EDTA | 0.04 |
| 6 | Brij 58 | 1.02 |
| 7 | Naloxone HCl 2H$_2$O | 0.98 |
| 8 | HPMC E5 | 5.0 |
| 9 | Water | 75.91 |
| TOTAL | — | 100.0 |

TABLE 4

(Example 4). Liquid Mixture Gel-B pH 9.5 for use with Naloxone 8 mg/g Gel A

| Ingredient | Ingredient | Amount (grams) |
|---|---|---|
| 1 | NaOH | 0.44 |
| 2 | NaHCO3 | 4.69 |
| 3 | Pluronic | 13.75 |
| 4 | HPMC E5 | 4.76 |
| 5 | Water | 76.36 |
| TOTAL | — | 100 |

TABLE 5

(Example 4). Naloxone 30 mg/g Liquid Gel-A, pH 3.5

| Ingredient Number | Name | Amount (grams) |
|---|---|---|
| 1 | Pluronic F127 | 14.20 |
| 2 | Sorbitol | 2.04 |
| 3 | Citric Acid | 0.38 |
| 4 | Na | 0.16 |
| 5 | EDTA | 0.04 |
| 6 | Brij 58 | 1.00 |
| 7 | Naloxone HCl 2H$_2$O | 3.68 |
| 8 | HPMC E5 | 4.00 |
| 9 | Water | 74.50 |
| TOTAL | — | 100.0 |

TABLE 6

(Example 4). Alkaline Buffer Gel-B pH 9.6 for use with Naloxone 30 mg/g Gel A

| Ingredient | Ingredient | Amount (grams) |
|---|---|---|
| 1 | NaOH | 0.48 |
| 2 | NaHCO3 | 5.16 |
| 3 | Pluronic | 13.66 |
| 4 | HPMC E5 | 4.76 |
| 5 | Water | 75.94 |
| TOTAL | — | 100 |

Results:

Administration of the test article was followed by complete recovery from fentanyl sedation in <6 minutes at doses of 30 mg; <8 minutes at 8 mg and >15 minutes at the 4 mg dose (see Table 7). Of the two control animals included in the study, one control animal was administered fentanyl but not subsequent administration of the test article. When no substantial improvement in fentanyl sedation was seen after 17 minutes, the animal was revived by IV naloxone injection. Another control animal was similarly sedated with fentanyl and administered the 8 mg gel without the corresponding buffer gel. After failure to recover from sedation, the animal was revived with IV naloxone injection after 18 minutes. These controlled experiments demonstrated effectiveness of the combined gel at completely reversing opioid agonist via the buccal route. Dose dependency of the responses was observed with the 4 mg/g formulation considerably slower than the 8 mg/g and 30 mg/g formulations in time to achieve complete reversal and recovery.

Blood from these animals was sampled at 3, 6, 10, 15, 30, 45, 60, 90, 120 and 240 minutes post dose and the plasma analyzed for naloxone using an un-validated method with an LLOQ of 0.1 ng/ml. As shown in FIG. 2, the rate of absorption was dependent on the drug concentration in the formulation. Maximum plasma concentration were seen between 15-45 minutes post dose for all animals. The highest dose/concentration (30 mg/g) formulation that showed very rapid and high absorption ($t_{max}$ of 15 minutes and $C_{max}$ of 853 ng/ml was chosen for further development.

TABLE 7

(of Example 4). Summary of Animal Study #16MUCOP1

| Animal ID | Fentanyl Dose Time | Fentanyl Dose (mg/kg) | Test Article Dose Time | Formulation | Time of Response | Time Elapsed (min:sec) |
|---|---|---|---|---|---|---|
| 2048516 | 9:33:01<br>9:40:28 | 0.025<br>0.010 | 9:42:42 | #1/#3-2 mL<br>(30 mg) | 9:48:00 | 5:18 |
| 2231230 | 10:33:36 | 0.030 | 10:41:54 | #2/#4-2 mL<br>(8 mg) | 10:49:00 | 7:06 |
| 2398673 | 11:03:15 | 0.030 | 11:13:04 | #2/#4-2 mL<br>(8 mg) | 11:21:00 | 7:56 |
| 2406072 | 11:45:12 | 0.030 | 11:50:56 | #2/#4-2 mL<br>(8 mg) | 11:58:00 | 7:04 |
| 2408300 | 12:13:25 | 0.030 | 12:20:13 | #2/#4-1 mL<br>(4 mg) | 12:39:00* | 18:47* |

*Animal bright, alert, and responsive but recumbent at 12:37:00; fully recovered at 12:39:00

The foregoing description of the present invention has been presented for purposes of illustration and description and is not intended to be exhaustive or to limit the invention to the precise form disclosed, and many modifications and variations are possible in light of the above teaching.

Example 5

Naloxone Gel Samples for Evaluation of Crystallization Inhibition

General Process for Preparing Sample Formulations A-E and Buffer Formulations 1&2 Naloxone Gel: Brij 58 and Naloxone were pre-dissolved in water using a magnetic stirrer. A dry blend of the remaining excipients were added slowly with rapid stirring. The mixture was placed in the refrigerator at 2-8° C. for 24 hrs. The samples were allowed to reach room temperature prior to testing.

Buffer Gel: Sodium hydroxide and sodium carbonate were pre-dissolved in water followed by the addition of the Pluronic F127. The mixture was manually stirred with a spatula in order to disperse the polymer. The samples were cooled for 24 hours at 2-8° C. for 24 hrs. The samples were allowed to reach room temperature prior to testing.

Combined Gel Testing: Naloxone base has very poor solubility in water (1.4 mg/mL), whereas the HCl salt is soluble at room temperature (RT) at greater than 70 mg/g in water. Naloxone HCl salt dissolved at above 1.4 mg/g of water at RT will instantly fall out of solution when buffer is added to neutralize the HCl and reach a basic pH. This is a rapid and conclusive test wherein the gel/solution immediately turns opaque when pH change occurs. The crystallization is confirmed by observation of the crystals using 100× magnification (See "Control" example in Table 10). Absorption of the active can only occur when the active is in solution—the rate of absorption of the un-ionized species of naloxone is much higher than that of the ionized species. A high proportion of naloxone exists as the unionized species at the boundary of the two pKa's for the drug—this occurs at a basic pH of around 9. However, as a basic buffer is added to the naloxone HCl solution, hydrochloride is immediately neutralized and the uncharged naloxone molecule instantly crystallizes and falls out of solution. The inclusion of certain polymeric crystallization can delay the crystallization of the drug to an extent and transiently maintain unionized naloxone in solution at a much higher concentration than its equilibrium solubility in a super-saturated state. The following test was conducted to observe the crystallization of naloxone under basic conditions and to note the impact of certain excipients on the delay (inhibition) of the crystallization from the super saturated solution. A delay of about 10 minutes is desired to enable sufficient absorption to occur; however, any duration of delay may be expected to be better than the instantaneous crystallization in the absence of a crystallization inhibitor.

Method: 1 gram of the Naloxone containing gel was added to a vial and 1 gram of the appropriate basic buffer gel was added over ~10 seconds. The two gels were mixed with a plastic spatula. A timer was initiated and the first sample (time zero) was observed for the existence of any crystals under an optical microscope at 100× magnification. Additional samples were taken at appropriate time intervals and observed for the presence of any crystals as shown in Table 10. The product is a rescue therapeutic; therefore, any delay in the appearance of crystals in the mixture is considered acceptable. Ten minutes or greater without the appearance of crystals is considered ideal. The pH was measured for samples and was around 9 for all samples. This pH is in the region where the highest fraction of unionized naloxone may be expected to exist.

Example 6

Inhibition of Crystallization in Naloxone Gel)

Several formulations of different compositions were prepared using the general methods described in example 5 with the intent of evaluating suitable excipients for the inhibition of naloxone crystallization after combination with an acidic buffer gel.

TABLE 8

(Example 6) Naloxone Drug Gel Samples

Nalaxone Drug Gel Sample Identifier

| Ingredient | A<br>All ingredients<br>% w/w | B<br>No HPMC<br>% w/w | C<br>No HPMC or F127<br>% w/w | D (Control)<br>No HPMC or F127 or Brij 58<br>% w/w | E<br>No F127 or Brij 58<br>% w/w |
|---|---|---|---|---|---|
| Sorbitol | 2.04 | 2.12 | 2.411 | 2.432 | 2.35 |
| Citric Acid | 0.38 | 0.395 | 0.449 | 0.453 | 0.438 |
| Sodium Citrate | 0.16 | 0.167 | 0.197 | 0.199 | 0.184 |
| Brij 58 | 1 | 1.04 | 1.182 | — | — |
| Naloxone HCl 2H$_2$0 | 3.68 | 3.837 | 4.51 | 4.56 | 4.34 |
| F127 | 14.2 | 14.768 | — | — | — |
| EDTA | 0.04 | 0.042 | 0.047 | 0.048 | 0.046 |
| HPMC E5 | 4 | — | — | — | 4.61 |
| Water | 74.5 | 77.63 | 91.204 | 92.308 | 88.032 |
| TOTAL | 100 | 100 | 100 | 100 | 100 |

TABLE 9

(Example 6). Buffer formulations 1 and 2 for use with Drug Gel Samples A, B, C, D and E

| Ingredient | Buffer Sample Number 1<br>% w/w | 2<br>% w/w |
|---|---|---|
| Sodium Hydroxide | 0.75 | 0.75 |
| Sodium Bicarbonate | 5.68 | 5.68 |
| F127 | 16.94 | — |
| Water | 76.63 | 93.57 |
| TOTAL | 100 | 100 |
| For use with Samples | A & B | C, D & E |

Evaluation of Naloxone crystallization inhibition after addition of Buffer 1 or 2 and the microscopic evaluation thereof is shown in Table 10. Crystals in combination C2 grew more slowly than combination D2 and suggests that some amount of crystallization inhibition due to presence of the surfactant, Brij 58 (polyoxyl 20 cetyl ether). However, combination D2 which does not contain a surfactant (neither Pluronic F127, nor Brij 58) and also no polymer (HPMC) appeared to be the least effective at inhibiting crystallization. Combination B1 at time zero did not show crystals; however within 5 minutes some small crystals were present. It appears that Pluronic F127 inhibited crystal growth for a short duration in combination B1. Combination A1 which contained F127, HPMC and Brij 58 showed no crystal growth for up to 10 minutes indicating a synergistic effect when using all excipients together. Applicant concluded that for some crystallization inhibition, at least one surfactant at a minimum is required with superior crystallization inhibition performance occurring with a surface active agent in combination with a cellulosic polymer.

TABLE 10

(Example 6). Microscopic Assessment Combined Gel Samples

| Time (Min.) | Sample A + Buffer 1 (A1) | Sample B + Buffer 1 (B1) | Sample C + Buffer 2 (C2) | Sample D + Buffer 2 (D2) (Control) | Sample E + Buffer 2 (E2) |
|---|---|---|---|---|---|
| 0 | No crystals | No crystals | Crystals | Crystals | Crystals |
| 5 | No crystals | Small crystals | Crystals | Crystals | Crystals |
| 10 | Small crystals | Increased crystals | Crystals | Crystals | Crystals |
| 15 | Increased crystal size | Increased number of small crystals with growth | Crystals | Crystals | Crystals |

Additional Crystallization Inhibition Experiments

Assessment of Naloxone crystallization inhibition in a formulation containing Carbopol 974. The formulation composition shown in Table 11 was prepared by adding 2 grams of the Carbopol formulation and mixing with 2 grams of Buffer 2 from Table 9 to obtain a pH near 8. Applicant mixed Carbopol formulation with Buffer 2 in a 1:1 ratio and observed under the microscope at 100× for crystal growth. No crystals were observed for up to 1 hour. Sample was held overnight and observed again. After 12 hours, there was no visible sign of crystallization at 100×. Applicant concluded that this formulation example with a gel former combined with a cellulosic crystallization inhibitor achieved longer term inhibition of crystallization of naloxone from a super saturated solution.

TABLE 11

(Example 6). Naloxone Gel Formulations Containing Carbopol

| Ingredient | Amt (g) | % |
|---|---|---|
| Naloxone HCl•2H$_2$O | 0.736 | 3.68 |
| HPMC E5 | 0.800 | 4.00 |
| EDTA | 0.200 | 1.00 |
| Citric Acid | 0.076 | 0.38 |
| Sodium Citrate | 0.032 | 0.16 |
| Sorbitol | 0.408 | 2.04 |
| Carbopol 974 | 0.540 | 2.70 |
| Water | 17.208 | 86.04 |
| TOTAL | 20.000 | 100.0 |

Example 7

Additional Excipients for the Inhibition of Naloxone Crystallization

Fifteen different composition of naloxone gels were made as shown in Table 12. These were combined with Buffer 2 from Table 9 and examined for naloxone crystals over time under the microscope. Table 13 shows the results from microscopic examination which demonstrates the ability to maintain a supersaturated solution at a pH which is conducive for absorption. As seen with the control example which does not contain surfactant, gel former, and polymeric crystallization inhibitor, the naloxone base falls out of solution instantaneously upon addition of the buffer. The best inhibition of crystallization of naloxone occurs when a gelling agent is combined with a polymeric crystallization inhibitor and/or surfactant. However, it is possible in some cases for the crystallization inhibitor to function both as the gelling agent and the inhibitor as seen with Pluronic F127 and Carbopol 974 (Carbomer). Some crystallization inhibitors can also function as gel formers and serve dual functions within the formulation.

TABLE 12

(Example 7). Additional Naloxone Gel Formulations with Polymeric Crystallization Inhibitors

| | Naloxone Gel Formulation | | | | | |
|---|---|---|---|---|---|---|
| | 1 % | 2 % | 3 % | 4 % | 5 % | Control % |
| Sorbitol | 2.04 | 2.04 | 2.04 | 2.04 | 2.04 | 2.432 |
| Citric Acid | 0.38 | 0.38 | 0.38 | 0.38 | 0.38 | 0.453 |
| Sodium Citrate | 0.16 | 0.16 | 0.16 | 0.16 | 0.16 | 0.199 |
| Brij 58 | 1 | 1 | 1 | 1 | 1 | — |
| Naloxone HCl 2H$_2$O | 3.68 | .3.68 | 3.68 | 3.68 | 3.68 | 4.56 |
| F127 | 13.87 | 13.87 | 13.87 | — | 13.87 | — |
| EDTA | 0.04 | 0.04 | 0.04 | 0.04 | 0.04 | 0.048 |
| HPMC E5 | — | — | 6 | 4 | — | — |
| HPMC E15 | — | — | — | — | — | — |
| HPC | — | — | — | — | — | — |
| VA64 | — | — | — | — | 6 | — |
| Soluplus | — | 6 | — | — | — | — |
| Affinisol E15 | 6 | — | — | — | — | — |
| Carbopol 974 | — | — | — | — | — | — |
| Carbopol 971 | — | — | — | 2.7 | — | — |
| Plasdone 29/32 | — | — | — | — | — | — |
| Acacia | — | — | — | — | — | — |
| Water | 72.83 | 72.83 | 72.83 | 86 | 72.83 | 92.308 |
| TOTAL | 100 | 100 | 100 | 100 | 100 | 100 |

| | Naloxone Gel Formulation | | | | |
|---|---|---|---|---|---|
| | 6 % | 7 % | 8 % | 9 % | 10 % |
| Sorbitol | 2.04 | — | 2.04 | 2.04 | 2.04 |
| Citric Acid | 0.38 | — | 0.38 | 0.38 | 0.38 |
| Sodium Citrate | 0.16 | — | 0.16 | 0.16 | 0.16 |
| Brij 58 | 1 | 1 | 1 | 1 | 1 |
| Naloxone HCl 2H$_2$O | 3.68 | 3.68 | 3.68 | 3.68 | 3.68 |
| F127 | — | 15 | 14.2 | 15.08 | 15.08 |
| EDTA | 1 | — | 0.04 | 0.04 | 0.04 |
| HPMC E5 | 4 | — | 3 | — | — |
| HPMC E15 | — | 1 | 1 | — | 2 |
| HPC JF | — | — | — | 2 | — |
| VA64 | — | — | — | — | — |
| Soluplus | — | — | — | — | — |
| Affinisol E15 | — | — | — | — | — |
| Carbopol 974 | 2.74 | — | — | — | — |
| Carbopol 971 | — | 2 | — | — | — |
| Plasdone 29/32 | — | — | — | — | 2 |
| Acacia | — | — | — | 2 | — |
| Water | 86.04 | 77.32 | 74.5 | 73.62 | 73.62 |
| Propylene Glycol | — | — | — | — | — |

| | Naloxone Gel Formulation | | | | |
|---|---|---|---|---|---|
| | 11 % | 12 % | 13 % | 14 % | 15 % |
| Sorbitol | 2.04 | 2.04 | 2.04 | 2.04 | 2.04 |
| Citric Acid | 0.38 | 0.38 | 0.38 | 0.38 | 0.38 |
| Sodium Citrate | 0.16 | 0.16 | 0.16 | 0.16 | 0.16 |
| Brij 58 | 1 | 1 | 1 | 1 | 1 |
| Naloxone HCl 2H$_2$O | 3.68 | 3.68 | 3.68 | 3.68 | 3.68 |
| F127 | 15.08 | 15.61 | 14.2 | 11.6 | 15.08 |
| EDTA | — | 0.04 | 0.04 | 0.04 | 0.04 |
| HPMC E5 | — | — | 3 | 3 | — |
| HPMC E15 | — | 3 | 1 | 1 | — |
| HPC JF | 4 | — | — | — | 4 |
| VA64 | — | — | — | — | — |
| Soluplus | — | — | — | 1 | — |
| Affinisol E15 | — | — | — | — | — |
| Carbopol 974 | — | — | — | — | — |
| Carbopol 971 | — | — | — | — | — |
| Plasdone 29/32 | — | 3 | — | — | — |
| Acacia | — | — | — | — | — |
| Water | 73.62 | 71.12 | 74.5 | 60.86 | 73.62 |
| Propylene Glycol | — | — | — | 15.23 | — |

TABLE 13

(Example 7) Microscopic Assessment of Crystallization Inhibition After addition of basic buffer

| Sample/Time (Mins) | 1 | 2 | 3 | 4 | 5 |
|---|---|---|---|---|---|
| 0 | No Crystals | No Crystals | No Crystals | No Crystals | No Crystals |
| 5 | No Crystals | No Crystals | No Crystals | No Crystals | No Crystals |
| 10 | No Crystals | No Crystals | No Crystals | No Crystals | No Crystals |
| 15 | Crystals | Crystals | Crystals | Crystals | Crystals |

| Sample/Time (Mins) | Control | 6 | 7 | 8 | 9 | 10 |
|---|---|---|---|---|---|---|
| 0 | Crystals | No Crystals | No Crystals | No Crystals | No Crystals | No Crystals |
| 5 | — | No Crystals | No Crystals | No Crystals | No Crystals | No Crystals |
| 10 | — | No Crystals | No Crystals | No Crystals | No Crystals | No Crystals |
| 15 | — | Crystals | Crystals | No Crystals | Crystals | Crystals |
| 20 | — | — | — | No Crystals | — | No Crystals |
| 40 | — | — | — | No Crystals | — | No Crystals |

| Sample/Time (Mins) | 11 | 12 | 13 | 14 | 15 |
|---|---|---|---|---|---|
| 0 | No Crystals | No Crystals | No Crystals | No Crystals | No Crystals |
| 5 | No Crystals | No Crystals | No Crystals | No Crystals | No Crystals |
| 10 | No Crystals | No Crystals | No Crystals | No Crystals | No Crystals |
| 15 | No Crystals | No Crystals | No Crystals | — | No Crystals |
| 20 | Crystals | No Crystals | No Crystals | — | No Crystals |

Useful crystallization inhibitors include, without limitation: HPMC (hydroxyl propyl methyl cellulose), HPC (hydroxyl propyl cellulose), Kollidon VA64 (Vinyl Pyrrolidone-Vinyl Acetate Co-Polymer), Soluplus (caprolactam/polyvinyl acetate/polyethylene glycol copolymer), Affinisol (HPMC with low glass transition temperature), Carbopol (Crosslinked polyacrylic acid polymer), Plasdone K29/32 (PVP Polyvinylpyrrolidone), Acacia (Gum Arabic), Brij 58 (Polyoxyethylene (20) Cetyl Ether), and F-127 (Kolliphor P407-Polyethylene/Polypropylene Glycol Co-Polymer Example 8

Co-Solvency, Permeation Enhancement, Mucoadhesion and Supersaturation

A combination of approaches may also be brought to bear to further improve the rate of absorption of the drug from the formulation. Specifically, in addition to the examples previously described, other solvents such as DMSO may be used in combination with water, to maintain the drug in solution as well as promote absorption though their inherent permeation enhancement properties. An example of such a formulation leveraging co-solvency and permeation enhancement is shown below in Table 14.

TABLE 14

(Example 8). Naloxone Gel formulation with co-solvent and polymers

| Ingredient | % w/w |
|---|---|
| Sorbitol | 2.02 |
| Citric Acid | 0.38 |
| Sodium Citrate | 0.16 |
| Brij 58 | 1 |
| Naloxone HCl 2H2O | 3.68 |
| F127 | 14.2 |
| EDTA | 0.04 |
| HPMC E5 | 4 |
| Polycarbophil (Noveon AA1) | 5 |
| DMSO | 25.0 |
| Water | 44.5 |
| TOTAL | 100.0 |

Example 9

Colorants/Dyes for Mixing and as a pH Indicator:

Proper mixing is critical for uniformity of pH once the two liquid gels are combined together. pH indicators may be used in the formulation to verify proper mixing by the end user. The following example demonstrates that the target pH was obtained during the mixing using a syringe and mixing tip as described in the parent application and shown in FIG. 5.

TABLE 15

(Example 9). Naloxone Gel formulation with pH indicator dye

| Ingredient | % w/w |
|---|---|
| Sorbitol | 2.02 |
| Citric Acid | 0.38 |
| Sodium Citrate | 0.16 |
| Dye | 0.02 |
| Brij 58 | 1 |
| Naloxone HCl 2H2O | 3.68 |
| F127 | 14.2 |
| EDTA | 0.04 |

TABLE 15-continued (Example 9). Naloxone Gel formulation with pH indicator dye

| Ingredient | % w/w |
|---|---|
| HPMC E5 | 4 |
| Water | 74.5 |
| TOTAL | 100.0 |

The example shown in table 15 is similar to Example 4 in this application with the additional inclusion of a pH-indicating dye. The dye used was an anthocyanin isolated from black carrot. This dye can function either as a pH indicator or mixing indicator and will turn from red at low pH to blue/violet color at basic pH or vice versa. As a test, one gram of the naloxone gel solution (Table 15) was placed in one chamber of a dual chambered syringe and one gram of the basic buffer gel (Table 2) was placed in the other chamber. The syringe was equipped with a spiral mixing tip. The syringe plunger was depressed and the two fluids mixed together as they exited the syringe tip. The color instantly changed from red to blue/violet. Applicant concluded that anthocyanins are instantaneous pH indicator dyes that visually confirm complete mixing of the gels to attain the desired basic pH. This is important for emergency responders and users to confirm that the active was properly administered at the point of use.

Example 10

Comparative Bioavailability Study of Naloxone Gel Formulations

Three formulations of naloxone buccal gel were employed in this study—Formulation 8, 9 and 14 from Table 12 in combination with Buffer system 1 from Table 9 to form the combined gel. Each formulation used a different type of crystallization inhibitor—formulation 8 used a combination of two molecular weight grades of HPMC, Formulation 9 used hydroxypropyl cellulose and Formulation 14 used Soluplus along with HPMC as well as propylene glycol as a co-solvent. The active Gel A formulation in each experiment had a concentration of 30 mg/g, and in each case an 8 mg dose of naloxone was administered (0.27 grams of a 30 mg/g Gel A). The basic buffer gel was also administered in the same amount for a combined gel weight of about 0.54 g. In each case, the naloxone gel was administered buccally in the left or right lower buccal cavity. In the case of formulation 14, the subjects were in supine position simulating an unconscious subject while formulation 8 and 9 were dosed with the subjects in the upright position. In all examples, the patient retained the gel in the mouth for twenty minutes after dosing placement followed by swallowing the mouth contents.

In each case, the following time pointes for blood draw were employed: pre-dose, and at 2.5, 5, 7.5, 10, 15, 20, 30, 45, 60, 120, 180, 240, 300, and 360 minutes. The study for formulation 9 was continued only until the 120 minute timepoint.

Blood plasma was separate via standard centrifuge procedure, and the naloxone concentrations in the plasma were determined using liquid chromatography-tandem mass spectrometry (LC-MS/MS) assay.

Figure 9:
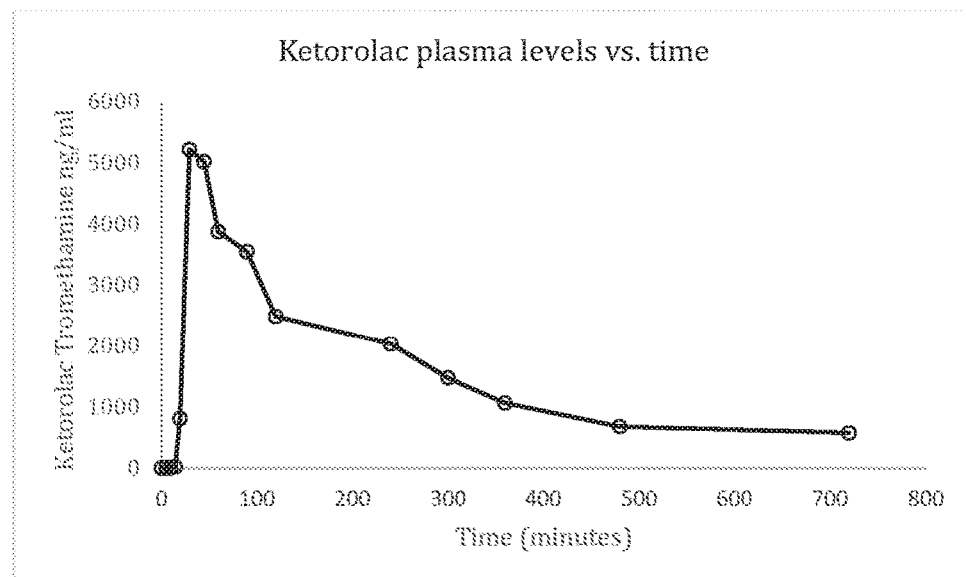
FIG. 9 is a graph of ketorolac plasma levels in a human study.

The results from the study are presented in FIG. 9. They are compared to results from intranasal naloxone administration (and intramuscular) from the pivotal study used to support approval of Narcan naloxone nasal spray in the reference source: Pharmacokinetic Properties and Human Use Characteristics of an FDA-Approved Intranasal Naloxone Product for the Treatment of Opioid Overdose. Krieter et al, J Clin Pharmacol. 2016 October; 56(10):1243-53. doi: 10.1002/jcph.759. Epub 2016 Jun. 10], the contents of which are incorporated herein by reference.

At a dose of 8 mg, the average Cmax of the applicant's gel formulation ranged from 5.3 to 8 ng/mL with Tmax ranging from 30 to 45 minutes. Applicant believes, based on this data (and other clinical results herein using different embodiment of the invention), that the results of this clinical study would correspond to the mean results of a larger study.

The formulation containing Soluplus appeared to have the best performance with the highest Cmax and shortest Tmax. These are surprising results in view of the fact that the buccal mucosa is widely acknowledged to be less permeable than the nasal mucosa. Buccal administration has major advantages over the nasal administration because certain conditions such as nasal septal abnormalities, nasal trauma, epistaxis, excessive nasal mucus from allergies or infections, and intranasal damage/injury from insufflation could dramatically impair absorption from the nasal mucosa. On the other hand, buccal absorption may be expected to be much more reliable. Applicant observed the buccal administration site is preferable to a sublingual site in view of the practical exigencies of administering a dose to a overdose patient. The buccal cavity is easier to access (closer), and does not require going past the patient's teeth nor manipulation of the patient's tongue. It is generally understood that the sublingual delivery is easier than buccal delivery, which makes Applicant's surprising results all the more remarkable.

Opioid agonist drugs may also be delivered by a similar approach for the treatment of pain.

Other Therapeutic Agents:

The parent application describes the use of a two gel system separated by a barrier and combined together at the point of use. However, the prior examples shown were for weakly basic actives that required alkaline pH for maximum uncharged species to exist to promote absorption. Examples 11 and 12 below demonstrate the inverse approach where a weakly acidic drug is maintained at an acidic pH after compounding to maximize absorption while optionally maintaining a basic environment for the active gel to keep it stable during storage. The active drugs chosen to illustrate this related but inverse approach are ketorolac tromethamine and diazepam.

Example 11

Ketorolac Gel and Bioavailability Study

Two distinct gels formulations were prepared in the manner described herein and shown in Table 16 and 17. Ketorolac Tromethamine (KT) was added to a mixture of water and PEG 400 and stirred to dissolve the drug. A dry blend of the remaining ingredients was mixed into the ketorolac solution. The mixture was refrigerated overnight to obtain a clear Gel A solution shown in Table 16 containing 40 mg/g of KT base. Tween 80, propylene glycol and water were mixed to obtain a solution. A dry blend of remaining ingredients was added with mixing to disperse the ingredients. The mixture was kept at room temperature to obtain a solution, Gel B at pH between 3 and 3.5.

1 g of KT-Gel was mixed in a vial with 1 g of acidic buffer and 1 gram of saliva. The final pH was measured as 3.5. No crystals were observed under a light microscope for at least 30 minutes after mixing the two gels.

TABLE 16

(Example 11). Ketorolac Tromethamine (KT) Gel A - 40 mg/g

| Ingredient | % | Amount (g) |
|---|---|---|
| Ketorolac Tromethamine | 5.92 | 1.480 |
| HPMC E5 | 3.25 | 0.812 |
| HPMC E15 | 1.25 | 0.312 |
| EDTA | 0.01 | 0.003 |
| Kolliphor P-407 (F-127) | 12.93 | 3.233 |
| Polyethylene Glycol 400 (PEG 400) | 15.08 | 3.770 |
| Water | 61.56 | 15.390 |
| Total | 100 | 25 |

TABLE 17

(Example 12). Acidic Buffer Gel B to obtain 3-3.5 pH

| Ingredient | % | Amount (g) |
|---|---|---|
| Citric Acid | 4.78 | 1.19 |
| Sodium Citrate | 0.51 | 0.13 |
| Tween 80 | 1.00 | 0.25 |
| Kolliphor P-407 | 15.08 | 3.77 |
| Propylene Glycol (PG) | 15.08 | 3.77 |
| HPMC E50 | 2.00 | 0.50 |
| Water | 61.55 | 15.39 |
| Total | 100 | 25 |

Human Bioavailability Study

An open label, single dose, pilot pharmacokinetic study was conducted on one healthy volunteer. The subject was orally administered a total dose of 40 mg of ketorolac gel (1 g of Gel A from Table 16 along with 1 gram of Gel B from Table 17. The combined gel was administered using a double barrel syringe similar to that shown in FIG. 12. Blood was drawn pre-dose and at 5, 10, 15, 20, 30, 45, 60, 90, 120, 180, 240, 480 and 720 minutes post-dose using Vacutainer® tubes containing sodium heparin. Plasma Ketorolac concentrations were determined using a non-validated liquid chromatography-tandem mass spectrometry (LC-MS/MS) assay.

Ketorolac is employed for treatment of post-surgical pain and also off-label for migraine rescue treatment, typically via intramuscular or intravenous injection. According to the prescribing information for Toradol® (Ketorolac Tromethamine), Tmax is achieved for oral Ketorolac (10 mg tablets) in 44±34 minutes whereas Tmax for intramuscular Ketorolac injection ranged between 33 and 44 minutes. The Cmax for a single dose 10 mg oral tablet was 0.87 µg/mL and for the intramuscular injection it was 1.14 µg/ml, 2.42 µg/mL and 4.55 µg/mL for the 15 mg, 30 mg and 60 mg respectively. See, www.accessdata.fda.gov/drugsatfda_docs/label/ . . . /019645s019lbl. pdf, the content of which is incorporated herein by reference.

Ketorolac is also available as an approved single dose strength (15.75 mg/spray) nasal spray formulation (Sprix®). The prescribing information shows that after administration of two 100 µL sprays (total dose 31.5 mg) the average Tmax for the nasal spray is 45 minutes with a range from 30 to 120 minutes. The Cmax was found to be 1.806 µg/mL with a standard deviation of 0.88. See https://www.accessdata.fda-.gov/drugsatfda_docs/nda/2010/022382_sprix_toc.cfm the content of which is incorporated herein by reference.

Applicant's gel formulation dosed at a 40 mg resulted in a Cmax of 5.2 µg/mL. Assuming dose proportionality of response and re-calculating the Cmax for an equivalent dose this amounts to 4.1 µg/mL at a 31.5 mg dose. Applicant believes based on this data (and other clinical results herein using different embodiment of the invention), that the results of this clinical study would correspond to the mean results of a larger study.

This is surprisingly superior with the Cmax more than twice that of the nasal spray. At an equivalent dose of 30 mg the Cmax for the gel is calculated to be 3.9 µg/mL which is also significantly better when compared to the 30 mg intramuscular dose which showed a Cmax of 2.42 µg/mL. The Tmax of the gel is also comparable to the approved intramuscular injection and superior to the approved oral and intranasal formulations. Preferably the Tmax is 25% faster than either of the oral or intranasal formulation, more preferably 35% faster, even more preferably 45% faster, most preferably 50% faster. Such Tmax may be achieved with embodiments of the present invention at any mucosal administration site.

The rapid uptake of ketorolac via the oromucosal route in the clinical study validates the inventiveness of the combined gel approach. Here, one chamber of the syringe contained the ketorolac solution and also included co-solvents, chelator, surfactant and polymers to attain a gel-like consistency. It exists at neutral to basic pH. In addition, it may also have permeation enhancers, antioxidants, a pH-indicating dye, and/or other components as described in this specification. The second chamber contained a citric-sodium citrate buffer in solution along with additional polymers, surfactants and co-solvents. When the two gels are combined as they are ejected through the mixing nozzle, the combined solution/gel pH is below 3.8. At this pH, the drug is significantly less soluble and therefore exists primarily as the protonated form and also exists at a concentration above saturation solubility. These two factors help to maximize absorption through the oral mucosa.

Other NSAID drug candidates that could be delivered by a similar approach: Mefenamic acid, naproxen, flurbiprofen, oxaprozin and diclofenac. These examples are non-limitative.

Example 12

Diazepam Gel and Bioavailability Study

Diazepam is indicated for the management of anxiety disorders, alcohol withdrawal, delirium tremens, agitation, tremor, hallucinosis, relief of skeletal muscle spasm, spasticity caused by cerebral palsy and paraplegia, athetosis, and adjunctively in convulsive disorders. Diazepam is commercially available as an oral tablet, oral liquid, injectable and rectal gel Diazepam has literature reported solubility in water of 50 µg/g of water and may therefore be expected to have practically no solubility at acidic pH. It is also well documented in the published literature that diazepam undergoes acid hydrolysis during storage and that stability and solubility are improved in non-aqueous solvent systems. However, the pH for the predomination of the maximally absorbable unionized form of diazepam is below its pKa of 3.4. Therefore, this molecule must ideally be formulated as a non-aqueous gel at a neutral pH for chemical stability and acidified to pH 3.4 at the point of use to maximize absorption. The example below illustrates the novel use of a combination approach of a supersaturation by dilution and spontaneous formation of an emulsion or microemulsion. See, Diazepam Water solubility 50 mg/Liter (at 25 degrees C.) Yalkowsky, S H & Dannenfelser, R M (1992) http:// www.drugbank.ca/drugs/DB00829; and Diazepam pKa=3.4 from Merck Index, the contents of which are incorporated herein by reference.

Applicant prepared a formulation of diazepam shown in Table 18 using the following method. Diazepam, TPGS (tocopherol polyethylene glycol succinate) and PG (propylene glycol) were mixed together and warmed to melt the TPGS and dissolve the diazepam and set aside as Pre-emulsion Gel A. Overnight, phase separation occurred but remixed with stirring to produce a translucent viscous liquid. When this pre-emulsion was added to water, a clear solution was obtained. Under a light microscope, the mixture appears to be a microemulsion. When 1 gram of diazepam pre-emulsion Gel A (Table 18) is added to 1 g of the acidic buffer (Table 19) and 1 g of human saliva, no drug crystals were observed under the microscope.

TABLE 18

(Example 12): Diazepam Pre-emulsion Gel A - 20 mg/g

| Ingredient | % | Amount (g) |
|---|---|---|
| Diazepam | 2.00 | 0.4 |
| Kolliphor-TPGS | 20.00 | 4.0 |
| Propylene Glycol (PG) | 78.00 | 15.6 |
| Total | 100 | 20 |

TABLE 19

(Example 12). Acidic Buffer Gel B pH 3-3.5

| Ingredient | % | Amount (g) |
|---|---|---|
| Citric Acid | 4.78 | 1.19 |
| Sodium Citrate | 0.51 | 0.13 |
| Tween 80 | 1.00 | 0.25 |
| Kolliphor P-407 | 15.08 | 3.77 |
| Propylene Glycol (PG) | 15.08 | 3.77 |
| HPMC E50 | 2.00 | 0.50 |
| Water | 61.55 | 15.39 |
| Total | 100 | 25 |

Discussion: Diazepam is poorly soluble in water (<0.05 mg/g). Diazepam is quite soluble in PG (>15 mg/g). In the pre-emulsion Gel A formulation a combination of PG is used with TPGS—diazepam is even more soluble >20 mg/g in this formulation. This does not exist as a supersaturated solution but a shelf-life stable solution at or below equilibrium solubility. The drug is formulated as a pre-emulsion that spontaneously emulsifies upon the addition of the acidic buffer to form a visually clear, isotropic microemulsion. When this pre-emulsion Gel A formulation is added to aqueous Gel B formulation, a microemulsion (or micellar solution of TPGS) is rapidly formed because the PG is very miscible with the water and immediately disperses into the acidic Gel B buffer. At this point, the drug that was quite soluble in PG is in a much less soluble system comprising of diluted PG (PG diluted with water and saliva)—however it remains briefly in solution due to the HPMC crystallization inhibitor and remains as clear isotropic system for 30 minutes or more. This 'supersaturation by dilution' allows the drug to remain in apparent solution at up to 10 mg/g without any microscopic evidence of crystal growth. A fraction of the drug stays within the non-polar micelles or mixed micelles or lamellar liquid crystal structures of TPGS and another fraction that is 'carried along' with the PG into the PG/water/saliva acidic solution. The system that is administered is therefore essentially a clear micellar microemulsion of a non-aqueous TPGS phase dispersed within a PG-water continuous aqueous phase. Here both the phases contain drug—the aqueous phase contains unionized drug at supersaturated concentration in an acidic environment and the non-aqueous phase also contains dissolved unionized drug. This combines a self-microemulsifying system with the combined gel system of extemporaneously mixing the drug solution with a pH adjusting acidic buffer to achieve a super saturated, microemulsion at the point of use. The dispersed internal phase of the microemulsion contains drug at high concentration.

The literature contains many references to a self-emulsifying drug delivery system wherein a lipidic self-emulsifying solution of drug is encapsulated within a softgel capsule where it is expected to emulsify when it comes in contact with the acidic stomach contents. However, mucosal absorption by extemporaneously forming the microemulsion prior to administration by combining with buffer to present the protonated drug species at the mucosal absorption surface is novel.

Human Bioavailability Study

An open label, single dose, pilot pharmacokinetic study was conducted on one healthy volunteer. The subject was orally administered a total dose of 5 mg of diazepam in combined gel (0.25 g of Gel A from Table 18 along with 0.25 gram of Gel B from Table 19). The combined gel was administered using a double barrel syringe similar to that shown in FIG. 5. Blood was drawn pre-dose and at 5, 10, 15, 20, 30, 45, 60, 90, 120, 180, 240, 480 and 720 minutes post-dose using Vacutainer® tubes containing sodium heparin. Plasma diazepam concentrations were determined using a non-validated liquid chromatography-tandem mass spectrometry (LC-MS/MS) assay.

Per the prescribing information (PI) for the diazepam tablet, after oral administration >90% of diazepam is absorbed and the average time to achieve peak plasma concentrations is 1-1.5 hours. In the presence of food mean lag times are approximately 45 minutes as compared with 15 minutes when fasting. There is also an increase in the average time to achieve peak concentrations to about 2.5 hours in the presence of food as compared with 1.25 hours when fasting. This results in an average decrease in Cmax of 20% when administered with food.

Figure 10:
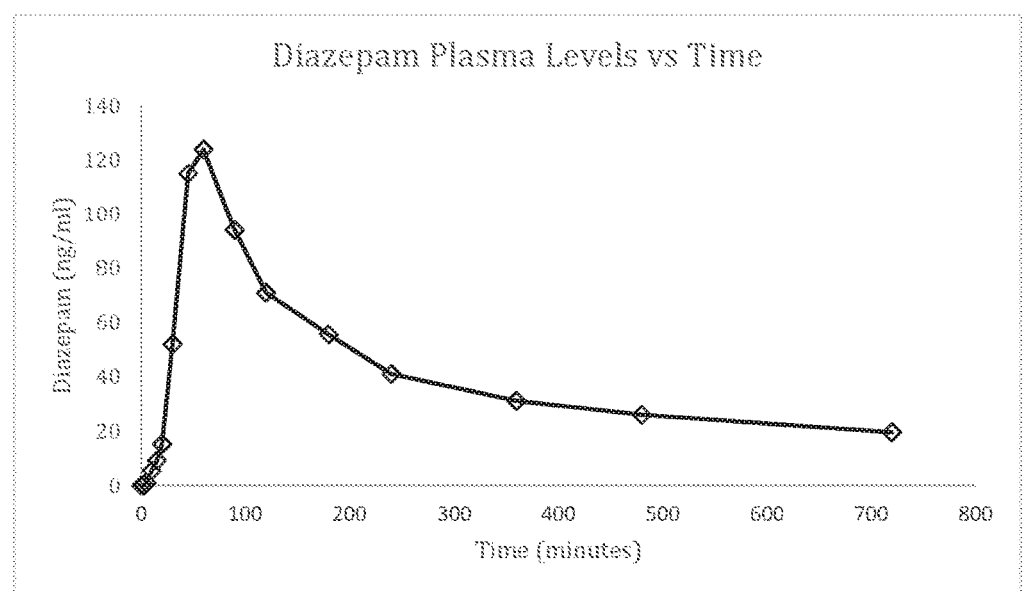
FIG. 10 is a graph of diazepam plasma levels in a human study.

Diazepam rectal gel is gel formulation of diazepam intended for rectal administration in the management of selected, refractory, patients with epilepsy on stable regiments of anti-epileptic drugs on who require diazepam intermittently to control bouts of increased seizure activity. Per the prescribing information (PI) for the diazepam rectal gel, the drug is well absorbed reaching peak plasma concentrations in 1.5 hours. The absolute bioavailability of the rectal gel relative to the injectable is 90%. The Cmax of after a 15 mg rectal dose is estimated from the graph provided in the PI to be about 380 ng/mL The pharmacokinetic performance of the applicant's diazaepam gel formulation is shown in FIG. 10. After buccal administration of a 5 mg dose the peak plasma concentration (Cmax) reached was 124 ng/mL. Assuming dose proportionality and adjusting for a 15 mg dose a theoretical Cmax of 372 ng/mL was comparable to the average rectal gel Cmax of 380 ng/mL. The Tmax of the buccal gel was 60 minutes which was comparable or superior to the oral tablet (1-1.5 hours) and the rectal gel (1.5 hours). Applicant notes the excellent Tmax, and further noted that compared with the ninety minute Tmax of the rectal gel, 70 minutes or less would be a substantial improvement but 60 minute Tmax demonstrated by the buccal gel of the present invention represented a substantial advance.

Applicant believes based on this data (and other clinical results herein using different embodiment of the invention), that the results of this clinical study would correspond to the mean results of a larger study.

The surprisingly rapid uptake of diazepam (Tmax in less than ninety minutes) via the oromucosal route in the clinic study validates the inventiveness of the combined gel approach for a less soluble pharmaceutical active. The harnessing of supersaturation by dilution and the formation of a self-emulsifying micellar or microemulsion system upon addition of acidic buffer allow rapid oromucosal absorption that has not been previously thought possible as evidenced by the absence of any marketed oromucosal products for this more than 60 year old drug. This is particularly important because the rapid absorption of a buccal gel is unaffected by whether the patient is in a fasted or fed state and also allows administration to unconscious epilepsy patients by a caregiver or self-administration by conscious patients for other indications.

Other anti-epileptic, anti-spasmodics, muscle relaxants and anxiolytic drugs candidates that can be delivered by a similar approach: Baclofen, Lorazepam, Midazolam, alprazolam, clonazepam, flurazepam, nitrazepam, chlordiazepoxide, triazolam etc.

Example 13: Naloxone Gel and Bioavailability Study

Applicant prepared a naloxone formulation as shown in Table 20 using the following procedure. Kolliphor RH40 was dissolved into water. Naloxone was added to the above solution and stirred until dissolved. The remaining ingredients were dry blended and added with mixing for 30 minutes. The mixture was stored in a refrigerator overnight at 4° C. to obtain clear viscous solution.

TABLE 20

| (Example 13) Naloxone 32 mg/g | | |
| --- | --- | --- |
| Ingredient | Amount (g) | % |
| Sorbitol | 0.51 | 2.04 |
| Citric Acid | 0.095 | 0.38 |
| Sodium Citrate | 0.04 | 0.16 |
| PEG-40 Castor Oil (Kolliphor RH40) | 0.25 | 1.0 |
| Hydroxypropyl cellulose (Klucel JF) | 1.0 | 4.0 |
| EDTA | 0.01 | 0.04 |
| Naloxone HCl•H$_2$O | 0.98 | 3.92 |
| Poloxamer P 407 (Kolliphor F127) | 2.5 | 10.0 |
| Water (DI) | 19.615 | 78.46 |
| Total | 25 | 100 |

A corresponding buffer formulation was prepared as shown in Table 21 using the following procedure. Sodium hydroxide and sodium bicarbonate were added to water and dissolved. Kolliphor was mixed into the solution for 30 minutes. The solution was stored in a refrigerator overnight to achieve a clear solution.

TABLE 21

| (Example 13) Buffer for Naloxone | | |
| --- | --- | --- |
| Ingredient | Amount (g) | % |
| Sodium Hydroxide | 0.375 | 0.75 |
| Sodium Bicarbonate | 2.84 | 5.68 |
| Poloxamer P 407 (Kolliphor F127) | 5 | 10 |
| Water (DI) | 41.785 | 83.57 |
| Total | 50 | 100 |

Observations:

Added 1 gram of Naloxone gel to 1 gram of Buffer gel to obtain pH 8.9. No crystallization was observed over 10 minutes and further dilution with 2 grams of water showed no precipitation.

Naloxone Bioavailability Study:

Naloxone Gel formulations shown in Table 20 and buffer shown in Table 21 were extemporaneously mixed in a 1:1 ratio and administered to healthy human subjects via the buccal, sublingual and intranasal routes at an 8 mg dose in a crossover study. A 0.4 mg intramuscular injection (commercially available naloxone solution) was administered as an injectable control. The data are shown in FIG. 11. The intranasal dose resulted in rapid absorption of the drug with a Cmax superior to that reported in the literature after intranasal administration of a simple naloxone solution (see Krieter et. al., *Pharmacokinetic Properties and Human Use Characteristics of an FDA Approved Intranasal Naloxone Product for the Treatment of Opioid Overdose* (J Clin Pharmacol. 2016 October; 56(10):1243-53. doi: 10.1002/jcph.759. Epub 2016 Jun. 10). The overall AUC after intranasal dosing was also significantly greater than buccal (for this example, to the inferior sulcus) or sublingual administration of the same gel formulation. Most notably, the time to reach maximum concentration was very rapid compared to buccal and sublingual dosing as well as literature reported values of tmax after intranasal dosing of a conventional solution.

Example 14

Nalbuphine Gel and Bioavailability Study

Nalbuphine is indicated for the relief of moderate to severe pain. It can be used for preoperative and postoperative analgesia, and for obstetrical analgesia during labor and delivery. Nalbuphine is a mixed opioid κ-agonist/μ-antagonist and is known to be about equi-analgesic on a mg basis to morphine. Nalbuphine is soluble in water up to about 35 mg/g and has a very low log P value of 1.4.

A nalbuphine containing gel was prepared as shown in Table 22. The flavors were mixed together and stirred into water. All other excipients were dry blended and added to above mixture with mixing for 30 minutes. Mixture was stored in a refrigerator at 4° C. overnight to obtain a clear solution.

A corresponding buffer formulation was prepared as shown in Table 23 using a similar procedure as in Example 13.

TABLE 22

| (Example 14) Nalbuphine 22.5 mg/g (Buccal) | | |
| --- | --- | --- |
| Ingredient | Amount (g) | % |
| HPMC E5 | 0.813 | 3.25 |
| HPMC E15 | 0.312 | 1.25 |
| Sucralose | 0.25 | 1.0 |

TABLE 22-continued (Example 14) Nalbuphine 22.5 mg/g (Buccal)

| Ingredient | Amount (g) | % |
|---|---|---|
| Flavor UA3361 (Ungerer) | 1.25 | 5.0 |
| Bittermask UA3359 (Ungerer) | 0.75 | 3 |
| Nalbuphine HCl | 0.62 | 2.48 |
| Poloxamer P 407 (Kolliphor F127) | 3.49 | 13.96 |
| Water (DI) | 17.515 | 70.06 |
| Total | 25 | 100 |

TABLE 23

(Example 14) Buffer for Nalbuphine (Buccal)

| Ingredient | Amount (g) | % |
|---|---|---|
| Sodium Hydroxide | 0.1870 | 0.75 |
| Sodium Bicarbonate | 1.425 | 5.7 |
| Kolliphor F127 | 5.0 | 20.0 |
| Water (DI) | 18.388 | 73.55 |
| Total | 25 | 100 |

A nalbuphine containing gel was prepared as shown in Table 24. All ingredients except Bittermask flavor were dry blended. The dry ingredient blend was added to water with stirring. Bittermask flavor was then added to the above solution with stirring. The entire mixture was stored overnight in a refrigerator at 4° C. to obtain clear viscous solution. A corresponding buffer formulation was prepared as shown in Table 25 using a similar procedure as in Example 13.

Observations:

One gram of above Nalbuphine examples were added to 1 gram of corresponding buffer to obtain pH~9. No crystallization was observed over 10 minutes and further dilution with 2 grams of water showed no immediate precipitation.

TABLE 24

(Example 14) Nalbuphine 28 mg/g (Intranasal)

| Ingredient | Amount (g) | % |
|---|---|---|
| HPMC E5 | 0.812 | 3.25 |
| HPMC E15 | 0.312 | 1.25 |
| Poloxamer P 407 (Kolliphor F127) | 1.25 | 5 |
| Bittermask UA3359 | 0.75 | 3 |
| Nalbuphine HCl | 0.776 | 3.1 |
| Water (DI) | 21.1 | 84.4 |
| Total | 25 | 100 |

TABLE 25

(Example 14) Buffer for Nalbuphine 28 mg/g (Intranasal)

| Ingredient | Amount (g) | % |
|---|---|---|
| Sodium Hydroxide | 0.375 | 0.75 |
| Sodium Bicarbonate | 2.84 | 5.68 |
| Poloxamer P 407 (Kolliphor F127) | 5 | 10 |
| Water (DI) | 41.785 | 83.57 |
| Total | 50 | 100 |

Nalbuphine Bioavailability Study:

An open label, single dose, pilot pharmacokinetic study was conducted on one healthy volunteer (buccal) and two healthy volunteers (intranasal). A subject was buccally administered a total dose of 20 mg of nalbuphine in a combined gel (0.89 g of Gel from Table 22 along with 0.89 gram of Gel from Table 23). The combined gel was administered using a double barrel syringe similar to that shown in FIG. 5. In another two subjects, a total dose of 16.8 mg of nalbuphine was administered nasally as a combined gel (0.6 g of Gel from Table 24 along with 0.6 g of Gel from Table 25).

Blood was drawn pre-dose and at 2.5, 5, 7.5, 10, 12.5, 15, 20, 30, 45, 60, 90, 120, 180, 240, (360) and (480) minutes post-dose within Vacutainer® tubes containing sodium heparin. Plasma nalbuphine concentrations were determined using a liquid chromatography-tandem mass spectrometry (LC-MS/MS) assay.

The concentration-time profiles are as shown in FIG. 12. The concentration-time profiles were analyzed using the non-compartmental analysis model of Phoenix® WinNonlin® 6.4.0.768. For comparison, dose-normalized PK parameters after i.v. and oral administration were used from Aitkenhead et al., *Br. J. Clin. Pharmac.* (1988) 25, 264-268 as summarized below:

TABLE 26

Pharmacokinetics after IV and Oral Administration (from Literature)

| Route | Dose [mg] | AUC/D [ng × mL$^{-1}$ × hr × mg$^{-1}$] | $t_{1/2}$ [min] | $Cl_{tot}/F$ [L × min$^{-1}$] | $t_{max}$ [min] | $C_{max}/D$ [ng/mL × mg] | F [%] |
|---|---|---|---|---|---|---|---|
| i.v. | 20 | 10.8 (6.6-18.4) | 222 (111-460) | 1.5 (0.8-2.3) | N/A | N/A | 1.00 |
| p.o. | 60 | 1.3 (0.5-2.3) | 279 (164-500) | 1.5 (0.8-2.3) | 46.6 (15.3-89.0) | 0.36 (0.10-0.60) | 0.12 (0.06-0.20) |

Model-independent PK parameters estimated for the one subject dosed with 20 mg of the nalbuphine gel intraorally are summarized below in Table 27. Model-independent PK parameters estimated for two subjects dosed with 16.8 mg of the nalbuphine gel intranasally are summarized below in Table 28:

TABLE 27

Pharmacokinetics after Buccal/Sublingual Administration

| Route | Dose [mg] | AUC/D [ng × mL$^{-1}$ × hr × mg$^{-1}$] | $t_{1/2}$ [min] | $Cl_{tot}/F$ [L × min$^{-1}$] | $t_{max}$ [min] | $C_{max}/D$ [ng/mL × mg] | F [%] |
|---|---|---|---|---|---|---|---|
| Buccal | 20 | 1.7 | 134 | 9.3 | 60 | 0.57 | 0.16 |

TABLE 28

Pharmacokinetics after Intranasal Administration

| Route | Dose [mg] | AUC/D [ng × mL$^{-1}$ × hr × mg$^{-1}$] | $t_{1/2}$ [min] | $Cl_{tot}/F$ [L × min$^{-1}$] | $t_{max}$ [min] | $C_{max}/D$ [ng/mL × mg] | F [%] |
|---|---|---|---|---|---|---|---|
| Intranasally | 16.8 | 2.8 (2.5-3.3) | 104 (98-110) | 5.3 (4.5-6.0) | 6.3 (5.0-7.5) | 1.7 (1.3-2.1) | 0.26 (0.23-0.31) |

PK parameters estimated after intranasal gel administration suggest that nalbuphine reaches the systemic circulation about 40 minutes faster than after oral or intraoral administration. Moreover, dose-normalized maximum drug plasma concentration is almost 5-fold greater after intranasal administration than measured after conventional oral administration implying more effective pharmacodynamic efficacy (i.e., pain relief). Estimated bioavailability after intranasal administration is almost twice of the value calculated for oral or intraoral administration despite a substantially greater total clearance. Reduced half-life correlates with increased total clearance. The data clearly demonstrate that intranasal administration of nalbuphine gel has the potential to extend the analgesic utility beyond institutional uses to ambulatory care. Further optimization of the formulation and larger number of study subjects may show further improved pharmacokinetic performance.

What is claimed is:

1. A kit for administering a mucosally absorbable composition to a human patient, comprising a first compartment comprising a first composition containing a substantially water-soluble pharmaceutical active agent comprising nalbuphine hydrochloride in a solution together with one or more optional suitable pharmaceutical excipients; and a second compartment comprising a second composition with one or more optional suitable pharmaceutical excipients, at least one of the first and second compositions containing an effective amount of a crystallization inhibitor; wherein the first and second compartments maintain separation of the first and second compositions during storage and allow for mixing of the first and second compositions to form a mucosally absorbable gel composition for immediate mucosal administration to a human patient to an intranasal site, wherein the second composition in the second compartment is at a basic pH and contains an alkaline buffer and the mucosally absorbable gel composition has a pH>7, and wherein the first and second compositions are configured to provide the nalbuphine hydrochloride in a state of supersaturation immediately after the mixing of the first and second compositions invoked by a rapid change in solubility effected by pH change.

2. The kit for administering a mucosally absorbable composition of claim 1, where the mucosally absorbable gel composition is a supersaturated solution for >10 minutes.

3. The kit of claim 1, wherein Tmax is achieved in less than twenty minutes when nalbuphine hydrochloride is administered intranasally.

4. The kit of claim 1, wherein Tmax is achieved in less than fifteen minutes when nalbuphine hydrochloride is administered intranasally.

5. The kit of claim 1, wherein Tmax is achieved in less than ten minutes when nalbuphine hydrochloride is administered intranasally.

6. The kit of claim 1, wherein bioavailability of nalbuphine hydrochloride of approximately or greater than 25% relative to parenterally administered drug is achieved when nalbuphine hydrochloride is administered intranasally.

7. The kit of claim 1, wherein Tmax is achieved in less than thirty minutes when nalbuphine hydrochloride is administered intranasally.

* * * * *